US012805919B2

(12) United States Patent
Chambers et al.

(10) Patent No.: US 12,805,919 B2
(45) Date of Patent: Nov. 24, 2026

(54) SURGICAL GUIDE WIRE ENGAGEMENT DEVICE

(71) Applicant: Axia Orthopedics, Inc., Portland, OR (US)

(72) Inventors: Casey M. Chambers, Boise, ID (US); Rebecca Schaldach, Portland, OR (US); James Michelinie, Portland, OR (US); Andrew William Seykora, Portland, OR (US)

(73) Assignee: Axia Orthopedics, Inc., Portland, OR (US)

(*) Notice: Subject to any disclaimer, the term of this patent is extended or adjusted under 35 U.S.C. 154(b) by 0 days.

(21) Appl. No.: 19/040,753

(22) Filed: Jan. 29, 2025

(65) Prior Publication Data

US 2025/0255653 A1 Aug. 14, 2025

Related U.S. Application Data

(63) Continuation of application No. 18/440,809, filed on Feb. 13, 2024, now Pat. No. 12,226,135.

(51) Int. Cl.
*A61B 17/84* (2006.01)
*A61B 17/88* (2006.01)
(Continued)

(52) U.S. Cl.
CPC .......... *A61B 17/844* (2013.01); *A61B 17/848* (2013.01); *A61B 17/8897* (2013.01); *A61B 2017/564* (2013.01); *A61B 2017/681* (2013.01)

(58) Field of Classification Search
CPC ... A61B 17/844; A61B 17/846; A61B 17/848; A61B 17/8897; A61B 17/885;
(Continued)

(56) References Cited

U.S. PATENT DOCUMENTS 3,809,075 A 5/1974 Matles
4,688,560 A 8/1987 Schultz
(Continued)

FOREIGN PATENT DOCUMENTS

CN 2009004163 U 7/2018
CN 109223145 A 1/2019
(Continued)

OTHER PUBLICATIONS

"International Search Report and Written Opinion", dated Mar. 21, 2025, from the counterpart PCT application PCT/US2025/012771.
(Continued)

*Primary Examiner* — Amy R Sipp
(74) *Attorney, Agent, or Firm* — John M. Rogitz; John L. Rogitz

(57) ABSTRACT

Medical devices are disclosed for compression of tissue and/or implants via a guide wire during provisional reduction in fracture fixation surgeries and other types of surgeries. Accordingly, an example device includes a housing with first and second apertures and a longitudinal axis. The device also includes a plate inside that itself includes a third aperture. The third aperture establishes a plane that is oblique with respect to the longitudinal axis while the plate is under spring bias from a spring in the housing. The spring helps maintain the oblique angle with respect to the longitudinal axis to lock the medical device at a desired position along the wire while the wire concurrently extends through the first, second, and third apertures. Methods for manufacturing, providing, and using the medical device(s) are also disclosed.

15 Claims, 35 Drawing Sheets

(51) Int. Cl.
*A61B 17/56* (2006.01)
*A61B 17/68* (2006.01)

(58) Field of Classification Search
CPC ............ A61B 17/8861; A61B 17/8866; A61B 17/8872; A61B 17/683; A61B 17/685; A61B 17/8019; A61B 17/8665; A61B 17/8685; A61B 17/8695; A61B 17/7092; A61B 17/1626; A61B 2017/681; A61B 2017/564; A61B 2017/565; A61B 2017/867
See application file for complete search history.

(56) References Cited

U.S. PATENT DOCUMENTS

| | | | | |
|---|---|---|---|---|
| 4,976,712 | A | 12/1990 | VanderSlik | |
| 5,009,134 | A | 4/1991 | Sorensen et al. | |
| 5,122,133 | A | 6/1992 | Evans | |
| 5,330,476 | A | 7/1994 | Hiot et al. | |
| 6,235,062 | B1 * | 5/2001 | Gramnas .................. | A61F 2/78 292/306 |
| 6,719,758 | B2 | 4/2004 | Beger et al. | |
| 7,517,350 | B2 | 4/2009 | Weiner et al. | |
| 7,833,225 | B2 | 11/2010 | Kay | |
| 8,679,167 | B2 | 3/2014 | Tipirneni et al. | |
| 8,758,350 | B2 | 6/2014 | Schmucki et al. | |
| 8,956,356 | B2 | 2/2015 | Zurschmiede | |
| 8,968,326 | B2 | 3/2015 | Mani et al. | |
| 9,060,809 | B2 | 6/2015 | Tipirneni et al. | |
| 9,089,378 | B2 | 7/2015 | Riemer et al. | |
| 9,364,275 | B2 | 6/2016 | Pacheco et al. | |
| 10,064,721 | B2 | 9/2018 | Lim et al. | |
| 10,561,457 | B2 | 2/2020 | Karadeniz | |
| 10,743,858 | B1 | 8/2020 | Cole et al. | |
| 11,432,860 | B2 | 9/2022 | O'Donald et al. | |
| 12,226,135 | B1 * | 2/2025 | Chambers ............ | A61B 17/685 |
| 12,611,321 | B2 | 4/2026 | Goldberg | |
| 2004/0097941 | A1 | 5/2004 | Weiner et al. | |
| 2008/0147127 | A1 | 6/2008 | Tipirneni et al. | |
| 2012/0165879 | A1 | 6/2012 | Khanna | |
| 2012/0203237 | A1 * | 8/2012 | Bryan .................... | A61B 90/06 606/102 |
| 2013/0030475 | A1 | 1/2013 | Weiner et al. | |
| 2013/0079776 | A1 * | 3/2013 | Zwirkoski ............ | A61B 17/683 606/62 |
| 2015/0374411 | A1 | 12/2015 | Ehmke et al. | |
| 2016/0242832 | A1 | 8/2016 | Castaneda et al. | |
| 2016/0338746 | A1 | 11/2016 | Scruggs et al. | |
| 2017/0360489 | A1 | 12/2017 | Palmer et al. | |
| 2018/0064473 | A1 | 3/2018 | Karadeniz | |
| 2021/0106369 | A1 | 4/2021 | Leak | |

FOREIGN PATENT DOCUMENTS

| | | | |
|---|---|---|---|
| CN | 213850982 | U | 10/2020 |
| CN | 219207244 | U | 1/2023 |

OTHER PUBLICATIONS

Seykora et al., "Apparatus for Advancing Surgical Guide Wire Engagement Device", file history of related pending U.S. Appl. No. 19/051,920, filed Feb. 12, 2025.

* cited by examiner

Example of Gradient Force Scale

Example of Quantitative Force Scale

SURGICAL GUIDE WIRE ENGAGEMENT DEVICE

FIELD

The disclosure below relates generally to surgical guide wire engagement devices for use in fracture reductions and other surgical procedures.

BACKGROUND

Kirschner wires (K-wires) are often used to aid in the alignment and provisional reduction of fractures and implants during fracture fixation surgery in a human patient. K-wires come in different diameters, lengths, and materials. They have at least one trochanteric drilling tip and in some cases a fluted tip. Some are smooth along the length and others have a threaded tip or ridges at the tip to improve bone purchase. K-wires help in orthopedic surgery as they create a very small hole that minimizes impact on the bone, thus allowing a surgeon several attempts at provisional reduction placement without significant bone loss. K-wires align bone fragments and implants in two planes of fixation.

However, one downside of K-wires is that they offer little to no compression (e.g., they do not align or compress in the third plane). Olive wires (OWs) and plate tacks (PTs) have been used to offer a slight improvement in reduction. Yet even here, the "olive" or "tack" is in a fixed position which prevents ideal wire purchase and/or depth. For threaded OW and PT, the bone thread interface often gets stripped because the wire is inserted at high speeds with a drill and advanced until the olive or tack is stopped by an implant or tissue, thus stripping the bone thread interface because the wire is still spinning but no longer advancing. One additional problem with OW and PT is that when inserted in a screw hole of a plate, a starting position off center will result in the olive or tack "kicking" the plate to the side as the olive or tack interacts with the plate hole.

There are also issues with locating and configuring a clamp to assist with provisional reduction, as this often requires another incision that is otherwise unnecessary. Also, the clamp might have to clamp down on other important and healthy bone, vascular structure, and nerve structure, which can damage those parts of the body. Clamps are also often quite crude in terms of the pressure they apply.

There are currently no adequate solutions to the foregoing problems.

SUMMARY

Accordingly, the disclosure below relates to technology that allows precise compression of tissue and/or implants over a K-wire, Steinmann pin, and/or other alignment mechanism during provisional reduction of fractures and implants during fracture fixation surgery in a human patient. A surgeon or other physician may thus verify an intended alignment, minimizing impact on the bone during provisional reduction placement without significant bone loss and prior to permanent reduction placement/fixation. Thus, the example devices discussed below may establish a movable pill or tack that can lock at any point along the K-wire, Steinmann pin, or other alignment wire/element.

Accordingly, in one aspect a medical device includes a housing with an elongated body. The housing defines a longitudinal axis. The housing includes a first end portion and a second end portion. The first end portion includes a first aperture while the second end portion includes a second aperture. The first aperture has a first height and first width establishing a first plane perpendicular to the longitudinal axis, and the second aperture has a second height and a second width establishing a second plane perpendicular to the longitudinal axis. The first and second planes are parallel to each other. The medical device also includes a plate disposed within the housing. The plate includes a third aperture having a third height and a third width establishing a third plane. The third plane is oblique with respect to the longitudinal axis while the plate is under spring bias from a spring in the housing. The first, second, and third apertures are at least partially aligned for a surgical guide wire to concurrently extend through the first, second, and third apertures while the plate is under spring bias from the spring. The spring bias is toward the first end portion. The spring is configured in the housing to impose the spring bias on the plate at a first area of the plate to help maintain the oblique angle of the third plane with respect to the longitudinal axis, and to impede withdrawal of the surgical guide wire from the third aperture toward the first aperture while the surgical guide wire extends through the third aperture. Additionally, a second area of the plate is configured within the housing to rest against a fulcrum within the housing. The plate is configured within the housing to rotate against a fulcrum during advancement of the surgical guide wire through the third aperture from the direction of the first aperture due to friction force during the advancement between the surgical guide wire and one or more plate portions around the third aperture. The friction force brings the third plane closer to parallel with the first and second planes. Still further, the medical device includes a release mechanism coupled to the housing. The release mechanism is manipulable to move the plate about a fulcrum to counteract the spring bias and permit withdrawal of the surgical guide wire from the third aperture toward the first aperture.

In some example embodiments, the spring may be a first spring. Here, the first end portion may include first and second telescoping members that slide with respect to each other according to the longitudinal axis. The first telescoping member may be more distal relative to the plate than the second telescoping member. The first telescoping member may be configured to slide toward the plate to compress a second spring on the housing that exerts force on the first telescoping member to push the first telescoping member away from the second telescoping member.

Also in some example embodiments, the housing may include a force gauge that indicates an amount of force the second spring exerts on the first telescoping member.

If desired, the housing may be at least partially cylindrical. Also if desired, a first distal external surface of the first end portion may be rounded to establish a convex first end of the housing. The first distal external surface may include the first aperture. A second distal external surface of the second end portion may be flat in a plane perpendicular to the longitudinal axis, and the second distal external surface may oppose the first distal external surface and include the second aperture.

In various example implementations, the release mechanism may include a slider that slides longitudinally along the housing to move the plate about a fulcrum to counteract the spring bias and permit withdrawal of the surgical guide wire from the third aperture through the first aperture. Additionally or alternatively, the release mechanism may include a lever coupled to the plate, where the lever may be manipulable to move the plate about a fulcrum to counteract the spring bias and permit withdrawal of the surgical guide wire from the third aperture through the first aperture. In some instances, the lever may be integral with the plate.

Also in example implementations, the housing may include a channel connecting the first, second, and third apertures for the surgical guide wire to concurrently extend through the first, second, and third apertures.

Still further, in some non-limiting examples the medical device may include a hand-held advancement mechanism. The housing may be couplable to the hand-held advancement mechanism to advance the housing along the surgical guide wire using the hand-held advancement mechanism while the surgical guide wire extends through the first, second, and third apertures.

Additionally, in some cases the first and second apertures may be circular. The first height and first width may thus both be measures of a first diameter of the first aperture, while the second height and second width may both be measures of a second diameter of the second aperture. What's more, if desired the third aperture may also be circular and, in such cases, the third height and third width may both be a measure of a third diameter of the third aperture. However, note that in other non-limiting examples one or more of the first, second, and/or third apertures may be oblong.

In some cases the medical device may also include the surgical guide wire.

Also note that if desired, the plate may be constrained/captured within the housing so that the third aperture remains at least partially aligned with the first and second apertures to receive the wire notwithstanding rotation of the plate within the housing. In another aspect, a device includes a housing with an elongated body. The housing defines a longitudinal axis. The housing includes a first end portion and a second end portion. The first end portion includes a first aperture. The second end portion includes a second aperture. The first aperture has a first height and first width establishing a first plane, and the second aperture has a second height and a second width establishing a second plane. The device also includes a first element disposed within the housing. The first element includes a third aperture. The third aperture has a third height and a third width establishing a third plane. The third plane is oblique with respect to the longitudinal axis while the first element is under bias from a second element in the housing. The first, second, and third apertures are at least partially aligned for a wire to concurrently extend through the first, second, and third apertures while the first element is under bias from the second element. The bias is toward the first end portion. The second element is configured in the housing to impose the bias on the first element at a first area of the first element to help maintain the oblique angle of the third plane with respect to the longitudinal axis, and to impede withdrawal of the wire from the third aperture toward the first aperture while the wire extends through the third aperture. A second area of the first element is configured within the housing to rest against a fulcrum within the housing. The first element is configured within the housing to rotate during advancement of the wire through the third aperture from the direction of the first aperture due to friction force during the advancement between the wire and one or more first element portions around the third aperture.

In some example embodiments, the device may also include a release mechanism coupled to the housing. The release mechanism may be manipulable to move the first element about a fulcrum to counteract the bias and permit withdrawal of the wire from the third aperture through the first aperture.

Additionally, in some examples the device may also include a hand-held advancement mechanism. The housing may be couplable to the hand-held advancement mechanism to advance the housing along the wire using the hand-held advancement mechanism while the wire extends through the first, second, and third apertures.

Still further, in some cases the first end portion may include first and second telescoping members that slide with respect to each other according to the longitudinal axis. The first telescoping member may be more distal relative to the first element than the second telescoping member. The first telescoping member may be configured to slide toward the first element to compress a third element on the housing that exerts force on the first telescoping member to push the first telescoping member away from the second telescoping member.

In still another aspect, a method includes providing a housing with an elongated body. The housing defines a longitudinal axis. The housing includes a first end portion and a second end portion. The first end portion includes a first aperture. The second end portion includes a second aperture. The first aperture has a first height and first width establishing a first plane, and the second aperture has a second height and a second width establishing a second plane. The method also includes providing a first element disposed within the housing. The first element includes a third aperture. The third aperture has a third height and a third width establishing a third plane. The third plane is oblique with respect to the longitudinal axis while the first element is under bias from a second element in the housing. The first, second, and third apertures are at least partially aligned for a wire to concurrently extend through the first, second, and third apertures while the first element is under bias from the second element. The bias is toward the first end portion. The second element configured in the housing to impose the bias on the first element at a first area of the first element to help maintain the oblique angle of the third plane with respect to the longitudinal axis, and to impede withdrawal of the wire from the third aperture toward the first aperture while the wire extends through the third aperture. A second area of the first element is configured within the housing to rest against a fulcrum within the housing. The first element is configured within the housing to rotate during advancement of the wire through the third aperture from the direction of the first aperture due to friction force during the advancement between the wire and one or more first element portions around the third aperture.

In some example instances, the housing and first element may be provided as part of a medical device. Here, the method may also include using the medical device and wire to maintain alignment of a first bone segment with another object during a surgical procedure. The other object may include a second bone segment and/or a surgical plate.

The details of the present application, both as to its structure and operation, can best be understood in reference to the accompanying drawings, in which like reference numerals refer to like parts, and in which:

DETAILED DESCRIPTION

Disclosed below are medical devices that allow compression of tissue and/or implants along a K-wire, Steinmann pin, and/or other alignment mechanism during provisional reduction of fractures in fracture fixation surgery for a human patient. Refined pressure of a desired amount may be applied using these devices, with the pressure being visually and tactilely demonstrated through one example device's sprung nose and force gauge. A surgeon or other physician may thus verify an intended bone alignment while reducing impact on the bone during provisional reduction, also minimizing significant bone loss that might otherwise occur prior to permanent reduction fixation. Accordingly, the example devices discussed below may establish a movable bead or tack that can lock at any point along a K-wire, Steinmann pin, or other alignment element due to an innovative collet/camming design, which may take an input force and create a force multiplier that bites into the wire harder and harder as force to withdraw the device from the wire continues to be applied (e.g., absent use of a release mechanism that may be used for withdrawal of the device from the wire as discussed further below).

Figure 1A:
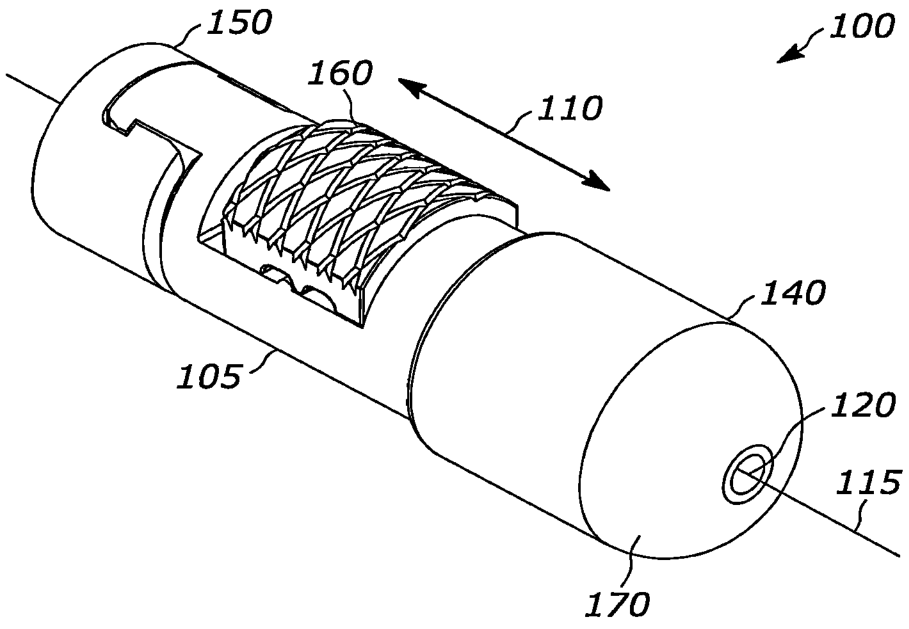
FIG. 1A shows a front isometric view of a first example embodiment of a medical device consistent with present principles.
Figure 1B:
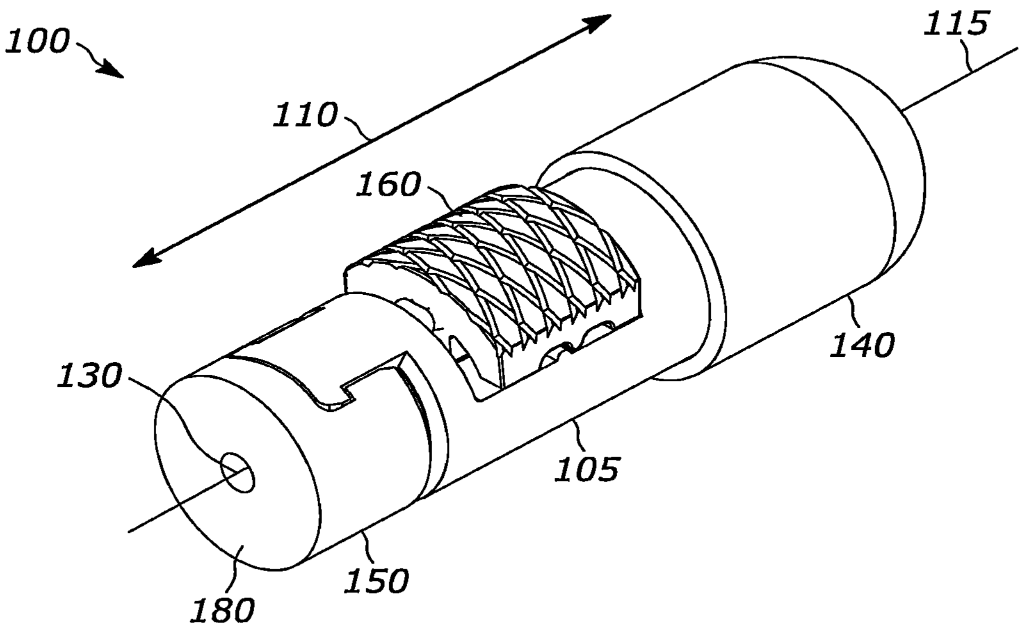
FIG. 1B shows a rear isometric view of the first example embodiment of the medical device consistent with present principles.

Beginning now in reference to FIGS. 1A and 1B, an example medical device 100 is shown respectively in front and rear isometric view. The device 100 may be used consistent with present principles to provide an input force at the nose of the device 100 and create a force multiplier at an aperture 260 of a cam plate 250 as described further below to bite down on a surgical guide wire 115, holding/locking the device 100 in place on the wire 115.

Accordingly, as shown in these figures, the medical device 100 may include a housing 105 with an elongated, rigid body. The housing 105 may be made of metal such as medical-grade steel or aluminum, for example. Additionally or alternatively, the housing 105 may be made of hard plastic, hardened polymer, and/or other suitable material. As also shown in these figures, the housing may define a longitudinal axis 110.

The housing 105 may be at least partially cylindrical as shown to avoid unintentionally catching on other body tissue in the area of the surgical site. The housing 105 may include a first end portion 140 of a first diameter as well as a second end portion 150 of a second diameter less than the first diameter. However, note that in other embodiments, the first and second diameters may be the same, or the second diameter may be more than the first diameter.

FIGS. 1A and 1B also show that in non-limiting examples, a first distal external surface 170 of the first end portion 140 may be rounded to establish a convex first end of the housing 105, with the first distal external surface 170 and/or portion 140 more generally including a first aperture 120. These two figures also show that a second distal external surface 180 of the second end portion 150 may be flat in a transverse plane perpendicular to the longitudinal axis 110, with the second distal external surface 180 and/or portion 150 more generally including a second aperture 130. However, in other non-limiting examples both distal external surfaces 170, 180 may be convex, or may be flat. Further note that the first and second distal external surfaces 170, 180 may face outward away from each other as shown.

The external surface(s) may be convex and rounded in non-limiting examples to prevent the device from inadvertently catching or grabbing other things in the surgical environment, which could in turn harm the patient. Also to prevent this from occurring, the exterior surfaces of the housing 105, including the surfaces 170, 180, may be smooth and/or have a polished finish.

FIGS. 1A and 1B also show that the apertures 120, 130 may be circular in height and width and cylindrical in depth. The apertures 120, 130 may have the same or different height/width diameters as each other. The first aperture 120 may therefore have a first height and first width establishing a first plane perpendicular to the longitudinal axis 110, and the second aperture 130 may have a second height and a second width establishing a second plane perpendicular to the longitudinal axis 110. In non-limiting examples, the first and second planes may be parallel to each other. The apertures 120, 130 may help constrain the surgical guide wire 115 as it extends through the device 100, as illustrated by FIGS. 1A and 1B.

During provisional fracture reduction, the device 100 may therefore receive the surgical guide wire 115 through the first aperture 120, with the wire 115 then being advanced through a hollow channel 240 and aperture 260 in the plate 250 (shown in the cutaway view of FIG. 3) to subsequently exit through the second aperture 130 such that the wire 115 then extends longitudinally through the entire device 100. Owing to the oblique angle of the aperture 260 as described in further detail below, the device 100 may then continue to be advanced down the wire 115 but may not be withdrawn from the wire 115 the opposite way save for manipulation of a release mechanism on the device 100.

Accordingly, FIGS. 1A-3 show one example release mechanism 160 that may be coupled to the housing 105, with the release mechanism 160 being a slider/button in this non-limiting example. The release mechanism 160 may be manipulable to move the metal or polymer plate 250 (or more generally, an element 250) inside the housing 105 about a fulcrum 300, with the fulcrum 300 shown best in FIG. 3. This action counteracts a spring bias/biasing moment exerted by a spring 230 inside the housing 105, permitting withdrawal of the surgical guide wire 115 from the third aperture 260 through the first aperture 120 so the device 100 may be removed from the wire 115 from the same direction from which it was advanced.

Figure 1C:
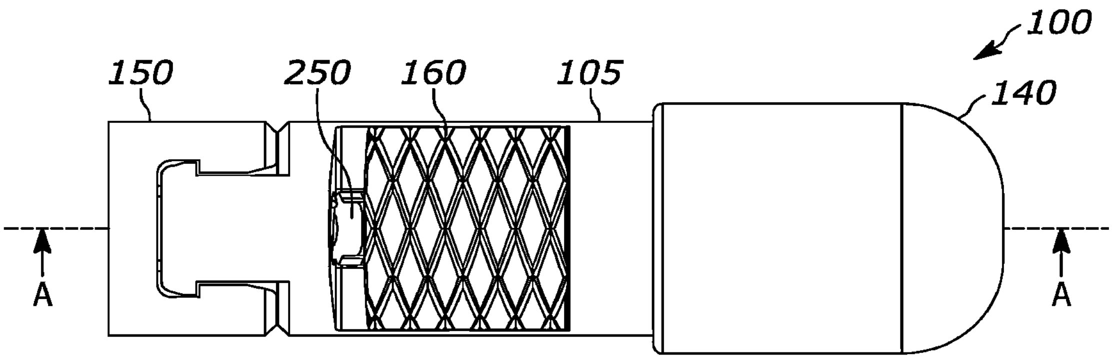
FIGS. 1C-1G show various orthogonal views of the first example embodiment of the medical device consistent with present principles.
Figure 1D:
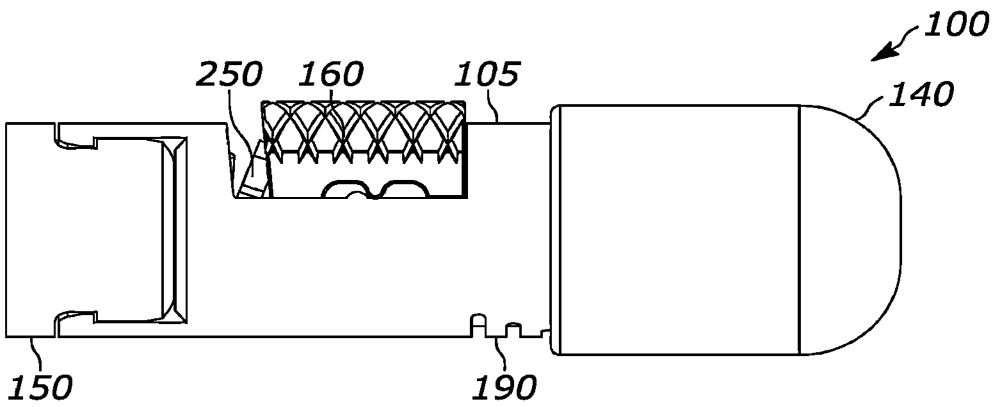
Figure 1E:
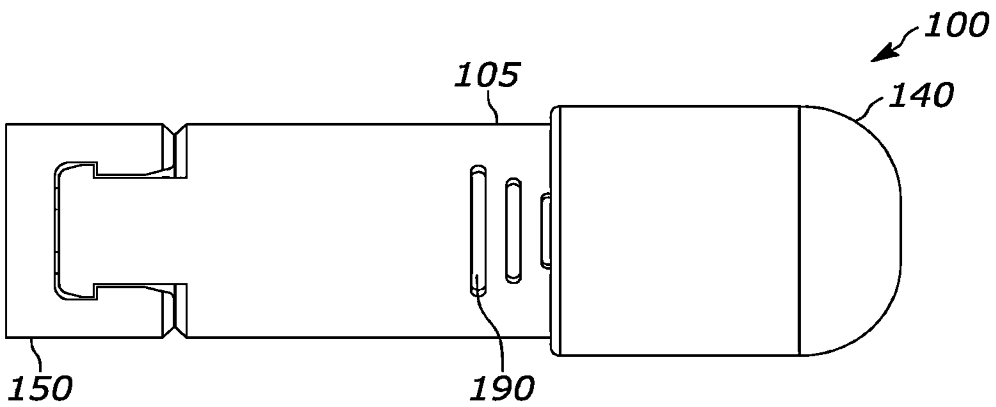
Figure 1F:
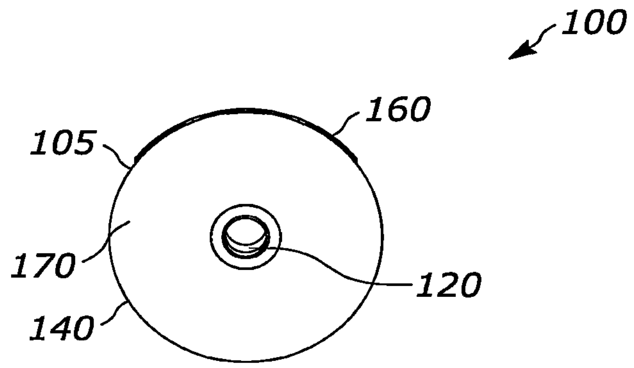
Figure 1G:
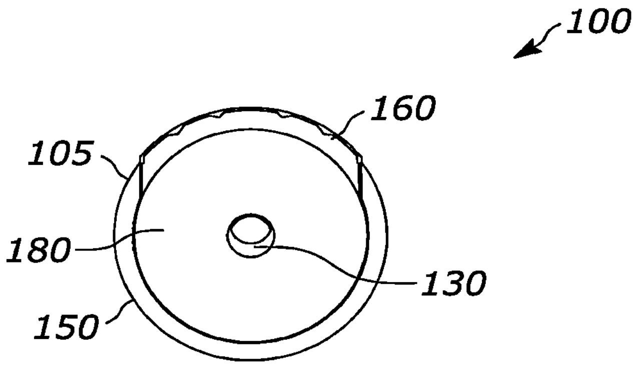

To further illustrate various aspects of the device 100, note that FIG. 1C shows the device 100 in top orthogonal view, while FIG. 1D shows the device 100 in side orthogonal view. FIG. 1E shows the device 100 in bottom orthogonal view. FIG. 1F shows the device 100 in front orthogonal view. FIG. 1G shows the device in rear orthogonal view.

Figure 2:
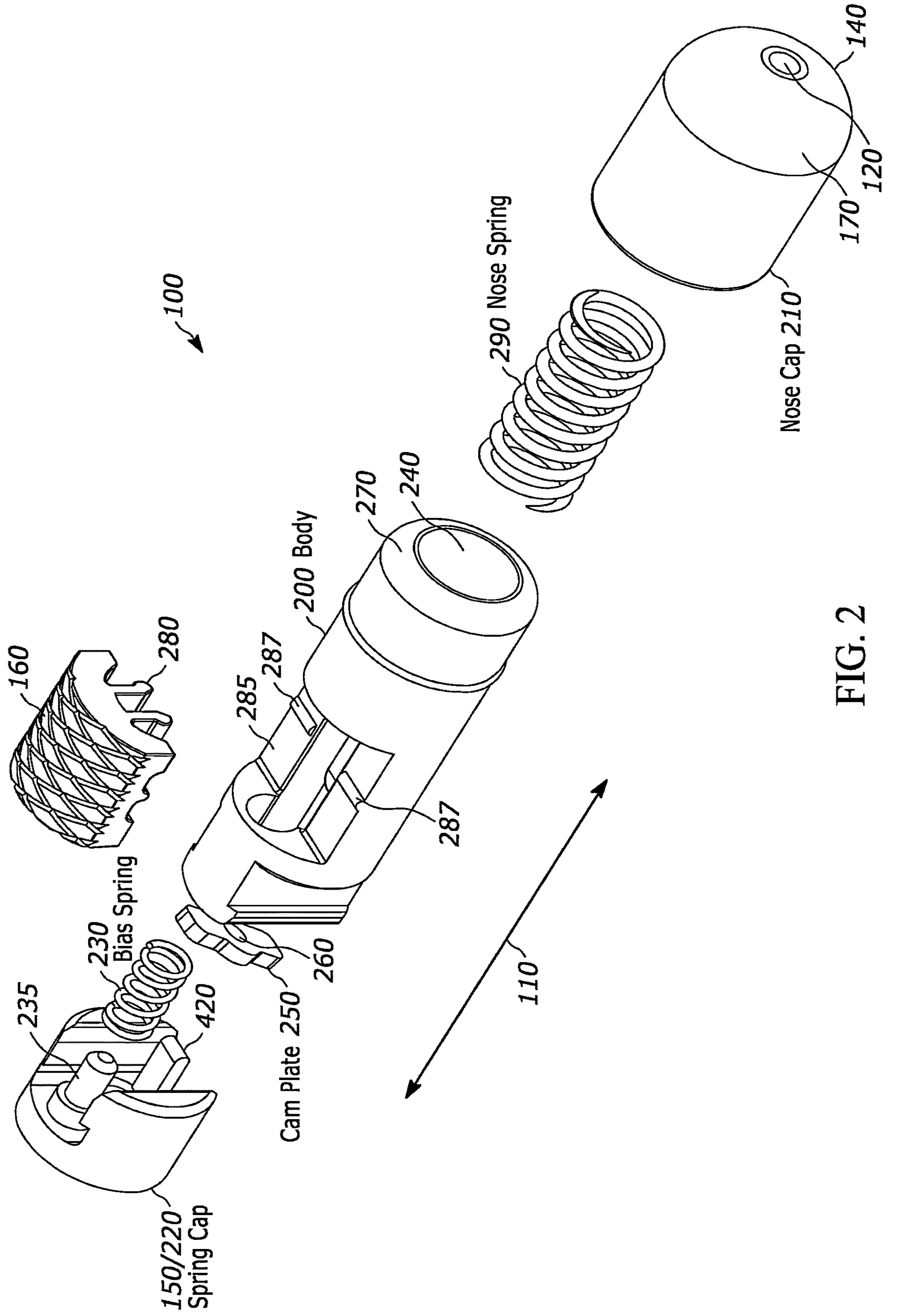
FIG. 2 shows an exploded view of the first example embodiment of the medical device consistent with present principles.

Additionally, FIG. 2 shows the device 100 in exploded view. As may be appreciated from this figure, the housing 105 includes a device body 200, front hollow nose cap 210, and rear spring cap 220. In non-limiting examples, the nose cap 210 may define some or all of the front end portion 140, while the rear spring cap 220 may define some or all of the rear end portion 150.

Figure 3:
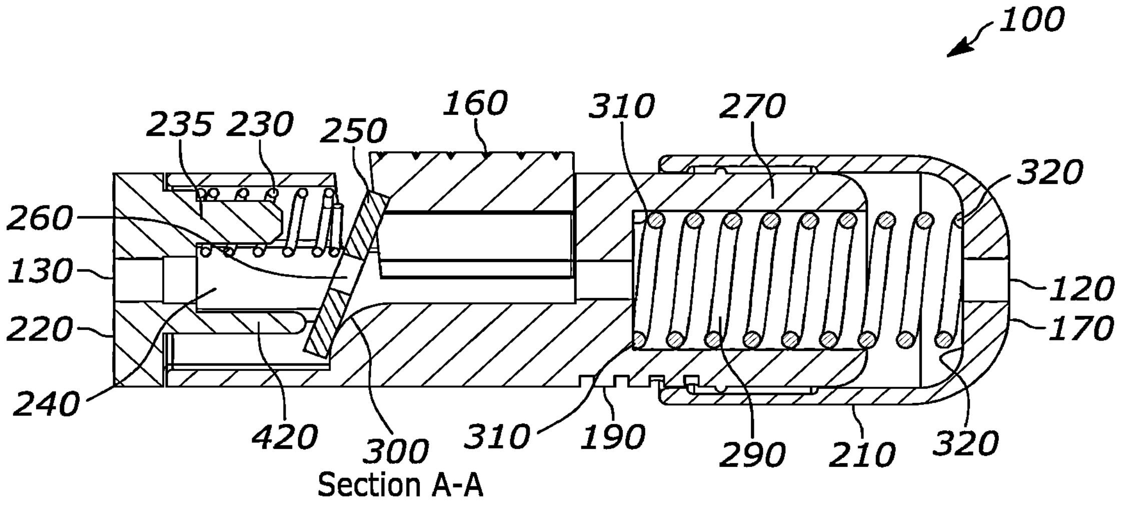
FIG. 3 shows a side cross-sectional view of the first example embodiment of the medical device consistent with present principles.

As also shown in FIG. 2 and further illustrated in the cross-sectional longitudinal side view of FIG. 3 (showing the device 100 as assembled), the device 100 may include the aforementioned cam plate 250 disposed within the housing 105. The cam plate 250 may include the third aperture 260. The third aperture 260 may have a third height and a third width establishing a third plane, where the third plane is oblique with respect to the longitudinal axis 110 while the plate 250 is under spring bias from the spring 230 in the housing 105. The oblique angle of the third plane (e.g., when the plate 250 is at rest under spring bias from the spring 230) may be between eighty five and twenty degrees relative to the longitudinal axis 110 in various non-limiting embodiments, and preferably eighty to fifty degrees and even sixty degrees in particular in specific non-limiting examples. Thus, as best shown in FIG. 3, the first aperture 120, second aperture 130, and third aperture 260 may be at least partially aligned for the surgical guide wire 115 to concurrently extend through the first, second, and third apertures while the plate 250 is still under spring bias from the spring 230 and obliquely oriented. The hollow channel 240 as shown in FIG. 3 may thus extend longitudinally through the transverse center of the housing 150 to fluidly connect the apertures 120, 130, and 200 for the wire 115 to concurrently extend through all three apertures and the channel 240 itself (despite the third plane of the third aperture 200 being oblique with respect to the longitudinal axis and hence not parallel to the first and second planes of the first and second apertures).

Describing the spring 230 in more detail, the spring 230 may be a compression spring (e.g., helical or conical) to oppose compression along the spring's longitudinal axis. However, other types of springs may also be used (e.g., leaf springs), and for that matter other types of elements configured for material bias may also be used in addition to or in lieu of a spring. For example, a semi-rigid polymer may be configured in a particular bowed shape to also exhibit a desired bias. But regardless of whether a spring or other type of biased element is used, note that the bias may be toward the first end portion 140 such that the spring/element 230 resists force/compression from the plate 250 toward the rear end portion 150. To this end, note that the distal segment of the spring 230 may be mounted onto a post 235. The post 235 may be made integral with the cap 200 and extend longitudinally within the housing 105 (e.g., parallel to the longitudinal axis 110). The proximal segment of the spring 230 may then be configured within the housing 150 to abut and impose the spring bias on the plate 250 at a first (upper) area of the plate 250 to help maintain the oblique angle of the third plane with respect to the longitudinal axis 110 and to therefore also impede withdrawal of the surgical guide wire 115 from the third aperture 260 toward the first aperture 120 while the surgical guide wire 115 extends through the third aperture 260.

Figure 4:
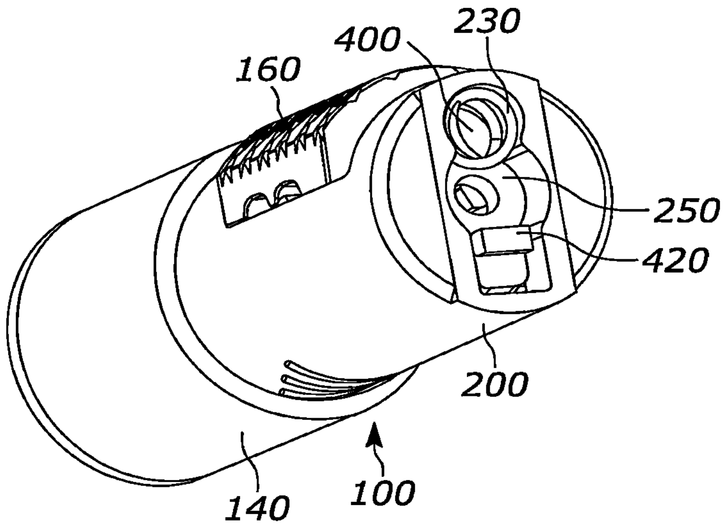
FIG. 4 shows a rear lower isometric view of the first example embodiment of the medical device consistent with present principles.

FIG. 4 is a rear isometric view that further illustrates, with it being noted that the rear spring cap 220 has been omitted to show the first area 400 of the plate 250 mentioned above (the area against which the spring 230 imposes the spring bias to help maintain the aforementioned oblique angle of the third plane). It may also be appreciated from FIG. 4 that the example plate 250 has a generally circular shape in the plate center that itself defines the third aperture 260. The plate 250 also has tabs extending up and down as shown. The upper tab establishes some or all of the first area 400 as generally facing toward the rear of the device. Additionally, the lower tab establishes some or all of a second area of the plate 250 as generally facing toward the front of the device 100. The second area is thus configured within the housing 105 to rest against the fulcrum 300 mounted or made integral with the housing 105. Accordingly, referring back to FIG. 3 for a moment, note that the fulcrum 300 may be established by an inner portion of the body 200 that is rounded from vertical to horizonal, device back to device front. However, further note that other fulcrum configurations are also encompassed by present principles.

Also note per FIG. 4 that the plate 250 is constrained not just by the fulcrum 300 but also by inner sidewalls of the housing 105 establishing an opening for the plate 250. This opening may therefore be shaped like the plate itself but may be slightly larger than the plate 250 to closely receive the plate 250 and constrain it from jostling sideways and up/down in an X-Y plane of the device 100 (the X-Y plane being perpendicular to the longitudinal axis and cutting transversely through the device 100). However, owing to their configuration, these cam plate constraint features still allow controlled radial/rotational movement of the plate 250 about the fulcrum 300 in the Z dimension. To further constrain the plate 250 while allowing this controlled movement, a longitudinally-extending element 420 on the cap 220 may abut the rear-facing portion of the lower tab of the plate 250, where the elements 420 and 300 form a pocket or hinge helping to maintain alignment of the apertures 120, 260, 130 even when the plate 250 is obliquely oriented.

It may be further appreciated from these figures that the plate 250 is configured within the housing 105 to rest against the element 420 and counteract the bias from the spring 230 during advancement of the wire 115 through the third aperture 260 from the direction of the first aperture 120. This plate resting against the element 420 during advancement is effected due to the friction force that is created between the wire 115 and plate portions around the aperture 260 as the device 100 is advanced down the wire 115. Accordingly, the friction force rotates the third plane of the third aperture 260 closer to parallel with the first and second planes to the first and second apertures 120, 130.

Based on the foregoing, it is to be even further understood that when the release mechanism 160 is activated, the release mechanism 160 unloads the plate 250/wire interface, with the plate 250 rotating within the pocket formed by fulcrum 420 and 300 to become more parallel. Thus, fulcrum 420 and 300 may both contain the plate 250 in the device 100 and form a point of rotation for plate rotation (e.g., when the release mechanism is active, moving the plate 250 closer to parallel). Thus, if the device 100 is holding load, that load is acting through fulcrum 300. Then to release the load, first the spring 230 is compressed until the plate 250/wire interface releases and then the plate may rotate and slide against the fulcrum 300. Accordingly, the structures of the elements 300 and 420 may together form a pocket or hinge point within which the plate can rotate.

Referring back to FIGS. 2 and 3 and further describing this pocket or hinge point created by the fulcrum 300 and element 420 of the device 100, the hinge point could instead be created by a pin and hinge assembly where a hole is formed cross-wise in the end near the second area of the plate 250 with an axis of this hole perpendicular to the longitudinal axis 110 of the device 100 and another hole formed in the body 200 such that it may be substantially aligned and concentric with the hole formed in the end of the plate 250. A pin made of metal or hard plastic or other substantially rigid and strong material may be positioned and assembled through these aligned holes in the plate 250 and body 200 to couple these components together and form a pinned-hinge connection.

Referring back to FIGS. 2 and 3 and describing other aspects of the device 100, the first end portion 140 of the device 100 may also include telescoping members that slide with respect to each other according to the longitudinal axis 110. In the present example, the nose cap 210 establishes one of the telescoping members and has a larger diameter than a second telescoping member 270 on the body 200 (though in other example embodiments the nose cap 210 may have a smaller diameter than the member 270 and telescope inside the body 200/member 270). The first telescoping member 210 is therefore distal to the plate 250 while the second telescoping member 270 is proximal to the plate 250.

As also shown in FIGS. 2 and 3, the first telescoping member 210 may be configured to slide toward the plate 250 to counteract bias from and compress a nose compression spring 290 on (e.g., in) the housing 105 that exerts force on the first telescoping member 210 to push the first telescoping member 210 distally away from the second telescoping member 270. The cross-sectional view of FIG. 3 thus illustrates that when the device 100 is assembled, the spring 290 extends longitudinally within the housing 105 so that it is coaxial with or at least parallel to the longitudinal axis 110, abutting one or more proximal walls 310 in the body 200 at the proximal end and abutting the inside front walls 320 of the hollow nose cap 210 at the distal end. Further note that the inside of the spring 290 may help establish some of the channel 240.

However, note that in other embodiments, the spring 290 may be located outside the housing body 200/member 270 such that the inner diameter of the spring 290 is greater than the outer diameter of the distal end of the housing (200/270). Additionally, in some examples the spring 290 may be integral with the housing 200/270.

Also note in terms of the distal nose cap 210 that it may be attached to the member 270 using a ring/rib on the external surface of the member 270 (circumscribing a transverse segment of the member 270) such that the nose cap 210 may be snapped over the ring/rib to couple to the member 270. The nose cap 210 may also have a relief region (e.g., of a greater diameter than the member 270) that allows telescoping movement but keeps the nose 210 attached to the body 200/270 such that it cannot slide distally off past the ring/rib.

The telescoping members 210, 270 and nose spring 290 are thus configured to reduce and absorb backlash in cam plate engagement with the wire 115, since slight wire travel within the device 100 can occur before the wire 115 gets cinched/bound in the third aperture 260 after advancement to a desired wire location. And to reiterate, once at the desired wire location, the device 100 may help maintain a compression force along the wire 115 between bone fragments and/or plates for ascertaining proper bone and/or plate alignment during fracture reduction or other bone repair (e.g., before much larger holes are drilled into the bone to insert screws or other fasteners for permanent fixation).

Thus, in one example, a physician may advance the device 100 up against the plate or bone, positioning the device 100 up against the plate/bone with slightly more compression force than ultimately desired to hold the device 100 at the desired wire position so that the telescoping elements may absorb the wire travel and ultimately hold the device 100 at the desired wire position with the desired amount of compression force. A force gauge 190 as also shown in various figures may further aid the physician in this task. In one example, the gauge 190 may be established by notches in an external surface of the body 200, where those notches provide an indication of the amount of force between cap 210 and body 200 due to the bias from the spring 290. Example force gauges 190*a* and 190*b* will be described in greater detail later in reference to FIGS. 5A and 5B.

But still in reference to FIGS. 2 and 3 and describing the one or more release mechanisms 160 in more detail, again note per the example shown that the mechanism(s) 160 include a slider button as shown. To slide longitudinally along the housing 105, the slider 160 may have a female track 280 mountable on a male track 285 on the body 200 to constrain the slider 160 from being removed up away from the body 200 and transversely across the body 200, while still permitting longitudinal movement along the combined track 280/285. Accordingly, when the device 100 is assembled as shown in FIG. 3, the rear portion of the slider 160 may abut the upper tab of the plate 250 such that a physician may take his/her finger(s) and slide the slider 160 back to rotate the plate 250 about the fulcrum 300. This action counteracts the spring bias from the spring 230 to bring the third plane of the third aperture 260 closer to parallel with the first and second planes to permit the wire 115 to be removed/withdrawn out of the first aperture 120 unencumbered by some or all of the cinch/binding action caused by the oblique angle of the third aperture 260 itself while the wire 115 extends through the third aperture 260. Also note that owing to the plate 250 having bias from the spring 230 exerted against it as described above, the slider 160 is also biased in a similar manner absent the physician sliding it back. However, further note that in some non-limiting examples, transverse ridges or ribs 287 on the upper portion of the track 285 may also receive reciprocal notches on the lower portions of the slider track 280 to provide some friction force to help maintain the slider 160 at a desired position on the track despite spring bias.

For completeness and before moving on to other figures, note that one or more of the body 200, cap 210, and/or cap 220 may be made integrally with each other, and/or may be engaged via snap fit, adhesive, etc. Either way, once coupled together, these components help to constrain the inner parts of the device 100 to bind and release the wire 115 from the third aperture 260 as desired to help with alignment of bone(s) (such as two bone fragments/segments of a same bone structure like a radius that is to be integral, absent fracture) and/or surgical plates prior to permanent fixation to ensure proper alignment before said permanent fixation.

Also before moving on to description of other figures, it is reiterated that while the first aperture 120, second aperture 130, and third aperture 260 may be circular as shown in the figures described above (with the respective height and width of each aperture both being measures of the respective diameter of the respective aperture itself), in other examples one or more of these apertures may be shaped differently if desired and depending on implementation. For example, one or more of the first, second, and/or third apertures may be oblong instead (e.g., oval-shaped with a long axis transverse to the longitudinal axis 110 sideways across the housing 150).

Figure 5A:
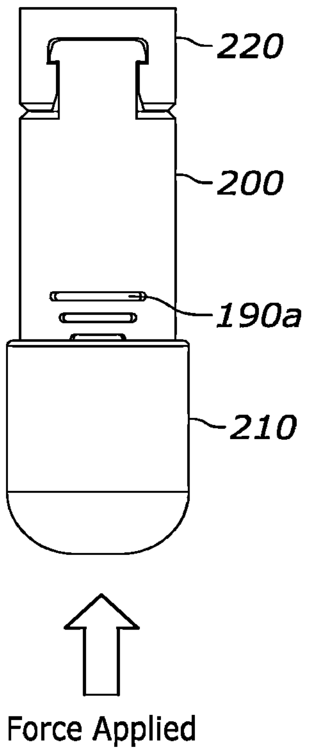
FIGS. 5A and 5B show orthogonal views of the first example embodiment of the medical device consistent with present principles to demonstrate different example force gauges that may be used.
Figure 5B:
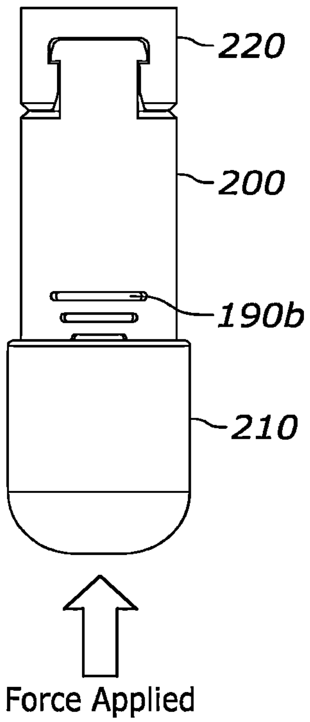

Now in reference to FIGS. 5A and 5B, two example implementations of the aforementioned force gauge 190 are shown, both of which may indicate an amount of force the second spring 290 exerts on the first telescoping member (cap 210). FIG. 5A shows an example gradient force scale/gauge 190*a* with line markings of increasing width for progressively increasing force, while FIG. 5B shows an example quantitative force scale/gauge 190*b* with increasing numbers for progressively increasing force.

Figure 6A:
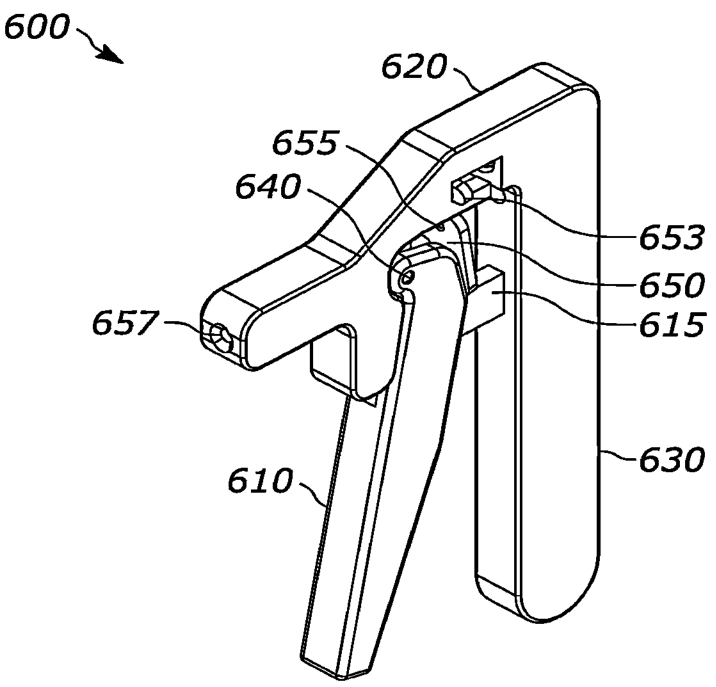
FIG. 6A shows a front isometric view of a first example embodiment of a hand-held advancement mechanism that may be used with the device of FIGS. 1-5B consistent with present principles.
Figure 6B:
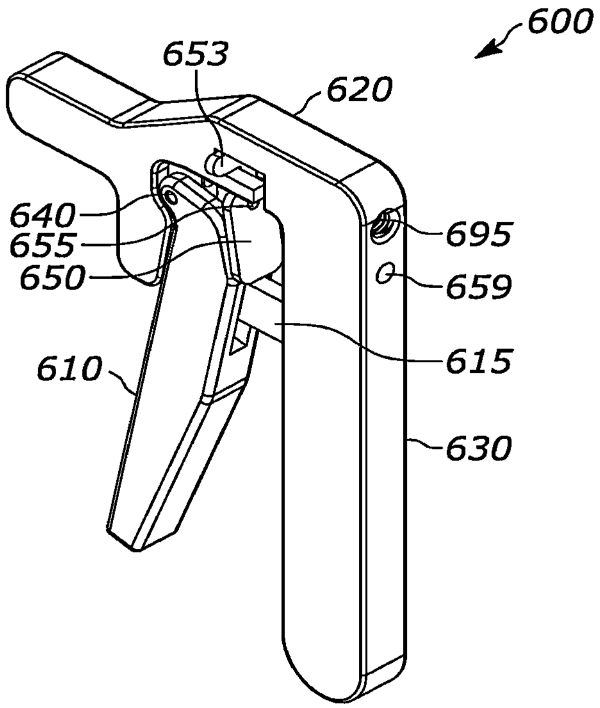
FIG. 6B shows a rear isometric view of the first example embodiment of the hand-held advancement mechanism consistent with present principles.
Figure 6C:
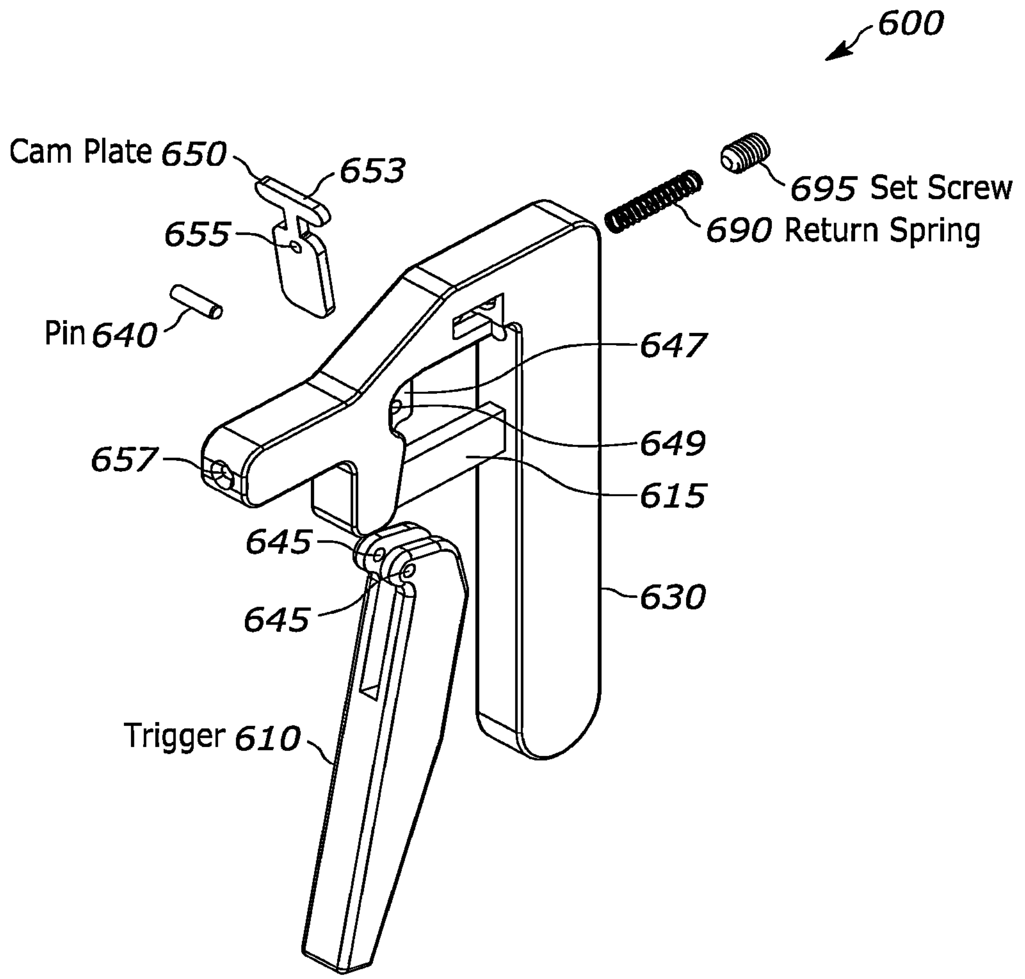
FIG. 6C shows an exploded view of the first example embodiment of the hand-held advancement mechanism consistent with present principles.

Continuing the detailed description in reference to FIGS. 6A-6C, an example hand-held advancement mechanism 600 is shown that may be used with the device 100 consistent with present principles. Specifically, FIGS. 6A-6B show front and rear isometric views of the mechanism 600, while FIG. 6C shows an exploded view of the mechanism 600. The mechanism 600 may establish a compression clamp assembly that may be used to help advance the device 100 along a surgical guide wire rather than doing so purely by hand (as also envisioned consistent with present principles). The mechanism 600 may therefore be helpful as it can be used to advance the device 100 along the wire in a more controlled manner, potentially while also using less force than advancement by hand alone due to the lever action of another cam plate in the mechanism 600. The housing 105 of the device 100 may therefore be advanced on the guide wire using a pull force implemented by the mechanism 600, whether the mechanism 600 is physically attached/coupled to the device 100 as shown in later figures or simply as it pushes the device 100 from behind according to the example embodiment of FIGS. 6A-6C.

As shown in FIGS. 6A-6C, the mechanism may generally be in the shape of a clamp gun and, as such, may include a rigid front arm/trigger 610 that rotates with respect to a rigid body 620 of the mechanism 600 while a rigid rear arm 630 remains immobile with respect to the body 620. In one particular example, the arm 630 may be made integral with the body 620, while the arm/trigger 610 may be coupled to another arm 615 that extends horizontally backwards from a lower vertical portion of the body 620 at the front of the body 620 to a front-facing vertical portion of the arm 630 at the rear of the body 620. Note that the elements 610, 620, and 630 may be made of metal such as medical-grade steel or aluminum, hard plastic, hardened polymer, and/or other suitable material.

As for the coupling of the arm 610 to the arm 615, this may be done via a metal or polymer pin 640 extending through opposing side holes 645 on the upper end portion of the arm 610, where the pin 640 also concurrently extends through an aperture 649 on a tab 647 on the body 620 (shown in the exploded view of FIG. 6C). In this way, the arm 610 is engaged with the body 620 for rotation of the arm 610 about the axis established by the length of the pin 640 (as extending transversely across the body 620) to rotate the arm 610 radially toward and away from the arm 630 about the pin axis.

This motion, in turn, results in force being exerted by a curved, rear-facing upper portion of the arm 610 on a metal or polymer cam plate 650 to move the plate 650 from its somewhat upright position or fully upright position as shown in FIGS. 6A and 6B (and FIG. 6D for that matter) to more oblique positions that slope progressively more from top to bottom, front to back. Additionally, note that the plate 650 has a circular or oblong guide wire aperture 655 for the surgical guide wire to extend through the aperture 655 as well as through a front aperture 657 and a rear aperture 659 on the mechanism 600. The apertures 657, 659 themselves may be circular or oblong.

Figure 6D:
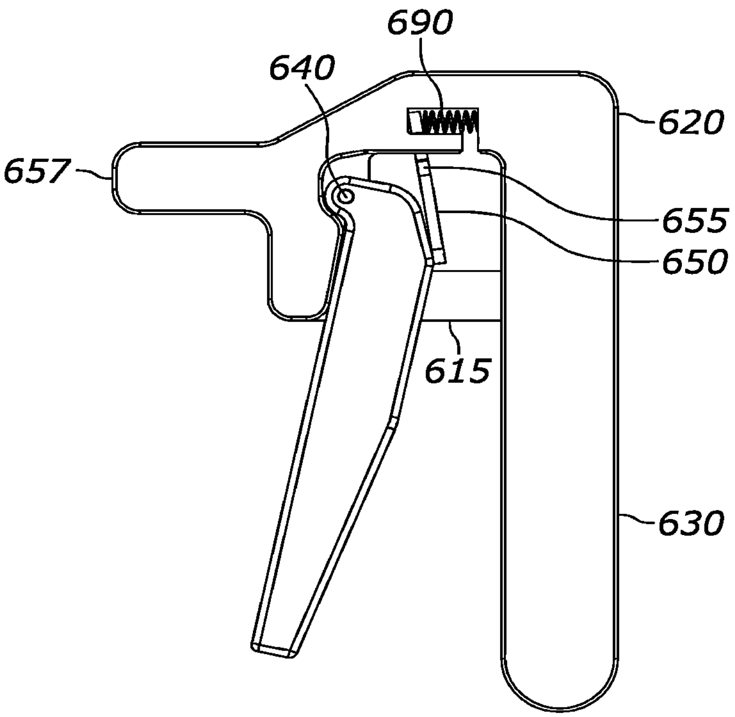
FIGS. 6D-6G show various orthogonal views of the first example embodiment of the hand-held advancement mechanism consistent with present principles.
Figure 6E:
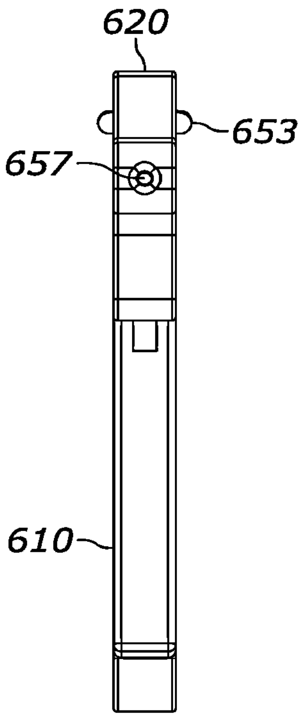
Figure 6F:
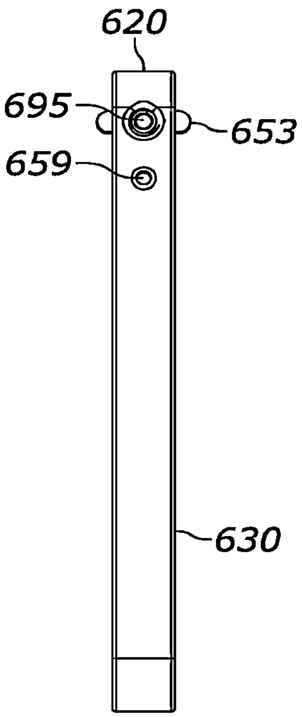
Figure 6G:
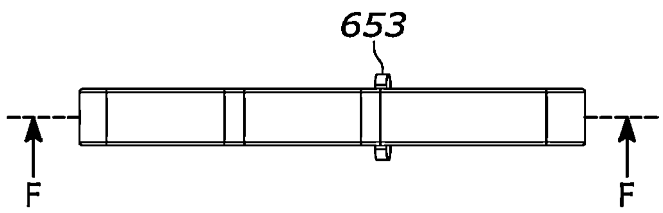
Figure 6H:
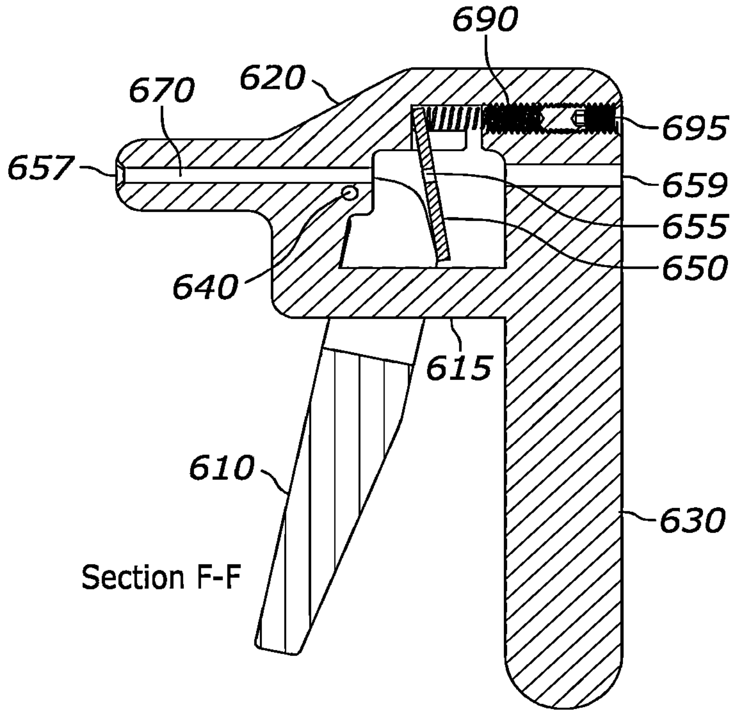
FIG. 6H shows a cross-sectional view of the first example embodiment of the hand-held advancement mechanism consistent with present principles.

Spring bias from a return spring 690 (such as a compression spring or other biased element) as disposed longitudinally in the body 620 therefore maintains the plate 650 in the somewhat upright position or fully upright position, allowing the wire to move freely through these three apertures on the mechanism 600 as well as through a channel 670 that both extends longitudinally through the body 620 and fluidly connects the apertures themselves (the channel 670 being shown in FIG. 6H). However, when the arm 610 is pulled back toward the arm 630, the portions of the plate 650 around the aperture 655 may grip the wire more and more as the plate 650 moves, advancing the mechanism 600 itself further down the wire. This counteracts the spring bias on the plate 650 in the process. Then when the arm 610 is released, the spring bias returns the plate 650 to its more upright position (and returns the arm 610 to its biased forward position in the process).

Describing the spring 690 in more detail, note that it may be anchored inside a receptacle in the body 620. As such the front end of the spring 690 may be anchored inside the body 620 itself while the back end of the spring 690 may be anchored to a set screw 695 that is screwed into the backside of the body 620.

The motion of the plate 650 as described above may therefore be used to advance the device 100 as located in front of the aperture 657 along the surgical guide wire, with the wire concurrently extending not just through the apertures and channel on the device 100 itself but also through the apertures and channel on the mechanism 600. The device 100 and mechanism 600 may thus be incrementally advanced forward together along the guide wire with each pull of the arm 610, with the mechanism 600 providing a pull action on the wire to move the device 100 forward and then the cam plate aperture 260 in the device 100 cinching the wire itself to hold the device 100 at its newly-advanced position.

Still in reference to FIGS. 6A-6C, further note that the plate 650 may also include a bar 653 on an uppermost portion, where the bar 653 extends laterally through the body 620 to expose distal portions of the bar 653 external to the body 620. Those distal portions of the bar 653 may help retain the plate 650 in place to ensure the aperture 655 is properly aligned for wire passage, also allowing rotation and translation of the plate 650. This structural feature 653 in combination with the surrounding housing of the body 620 may thus hold the plate 650 in its correct position.

Figure 6I:
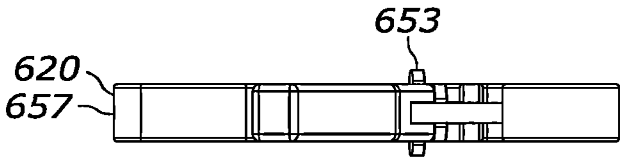
FIG. 6I shows another orthogonal view of the first example embodiment of the hand-held advancement mechanism consistent with present principles.

The orthogonal views of FIGS. 6D-I further illustrate. FIG. 6D is a side orthogonal view of the mechanism 600, FIG. 6E is a front orthogonal view of the mechanism 600, FIG. 6F is a rear orthogonal view of the mechanism 600, and FIG. 6G is a top orthogonal view of the mechanism 600. Additionally, FIG. 6H is a side cross-sectional view of the mechanism 600 while FIG. 6I is a top orthogonal view of the mechanism 600.

Figure 6J:
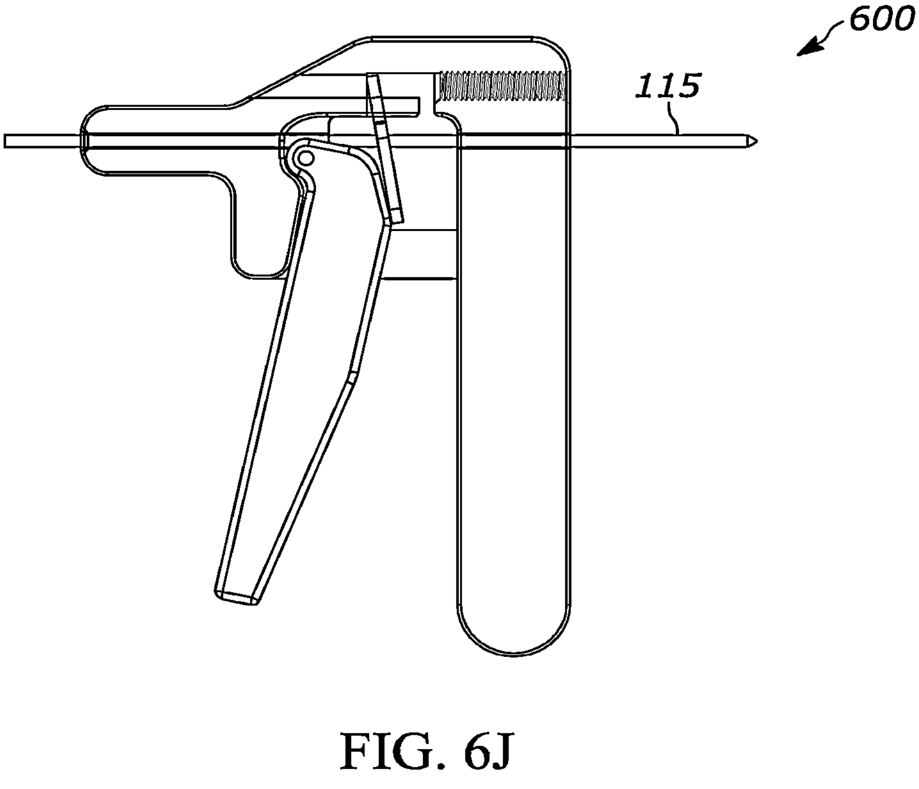
FIGS. 6J and 6K show cutaway views of a wire extending through apertures and a channel of the first example embodiment of the hand-held advancement mechanism consistent with present principles.
Figure 6K:
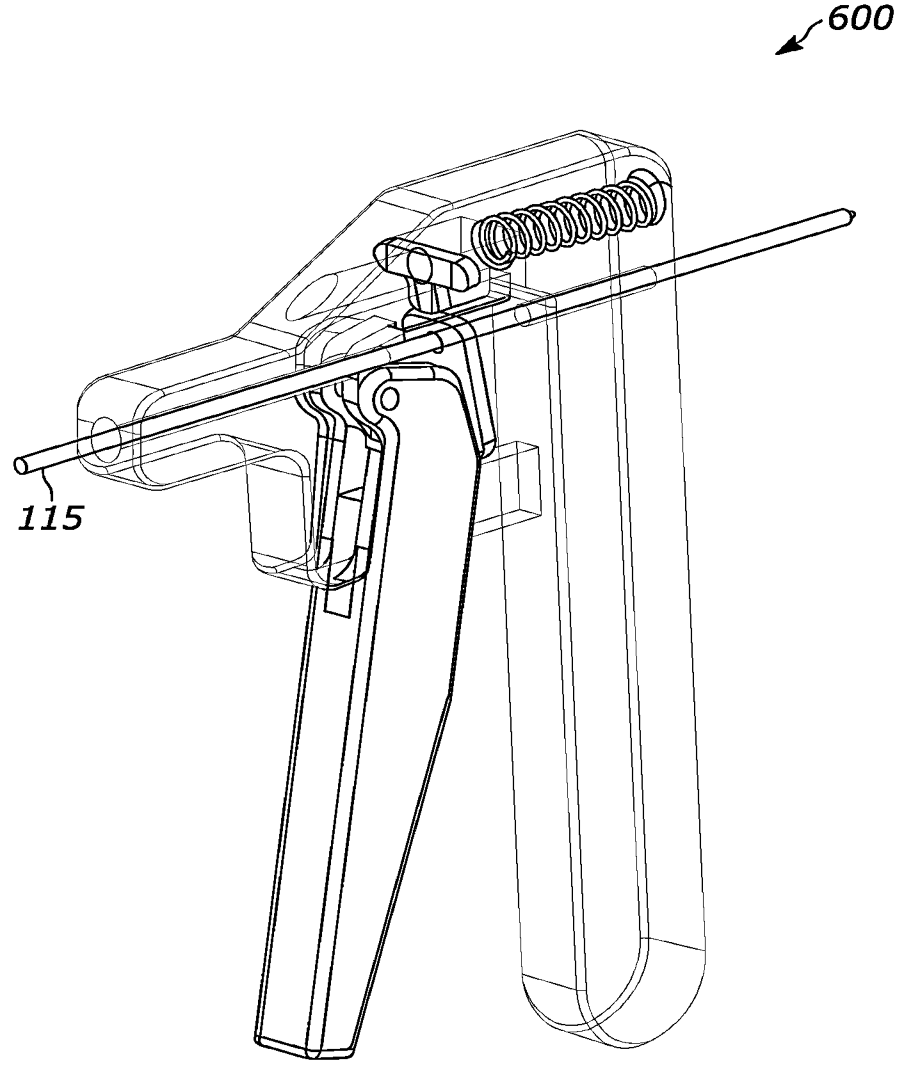

Particularly in reference to FIG. 6H, note that the apertures 657, 655, and 659 are connected through the aforementioned hollow channel 670 aligned with the apertures 657, 655, and 659 so that the surgical guide wire can concurrently extend through the apertures 657, 655, and 659 and channel 670 during advancement as described above. Also note that FIG. 6J shows an orthogonal cutaway side view of the wire 115 extending through the apertures/channel of the mechanism 600, while FIG. 6K shows an isometric cutaway view of the wire extending through the apertures/channel of the mechanism 600.

Figure 7A:
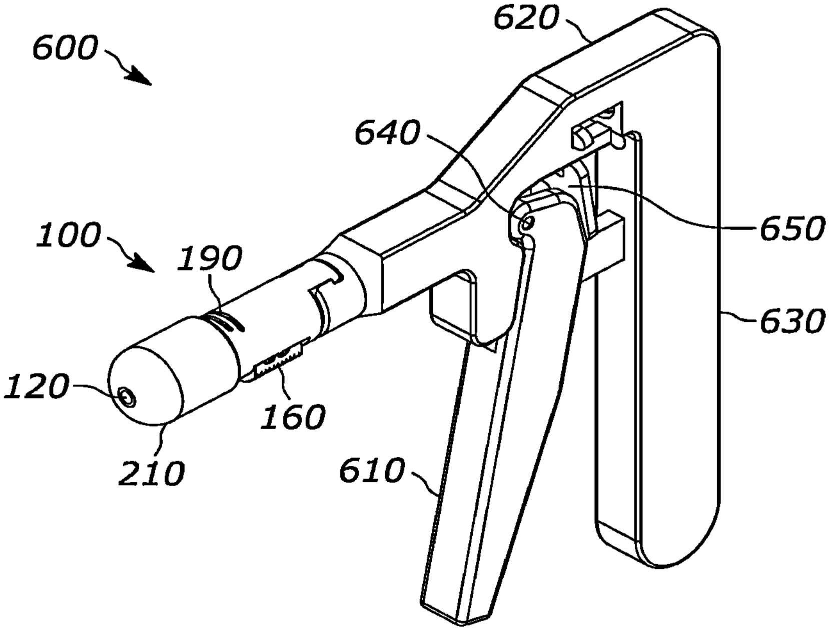
FIG. 7A shows a front isometric view of a second example embodiment of the hand-held advancement mechanism consistent with present principles.
Figure 7B:
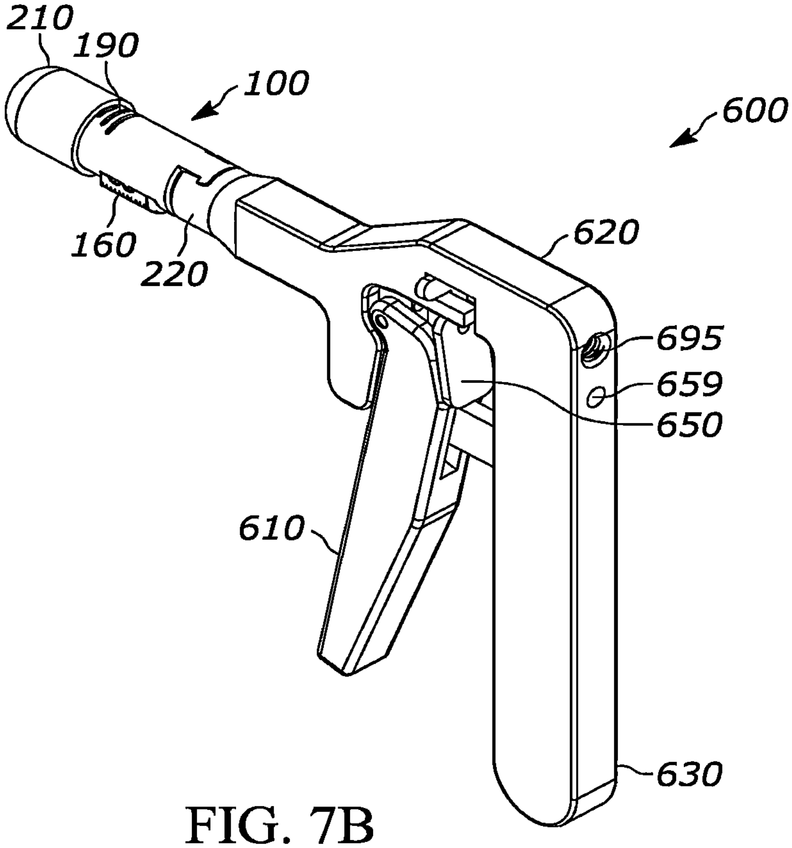
FIG. 7B shows a rear isometric view of the second example embodiment of the hand-held advancement mechanism consistent with present principles.
Figure 7C:
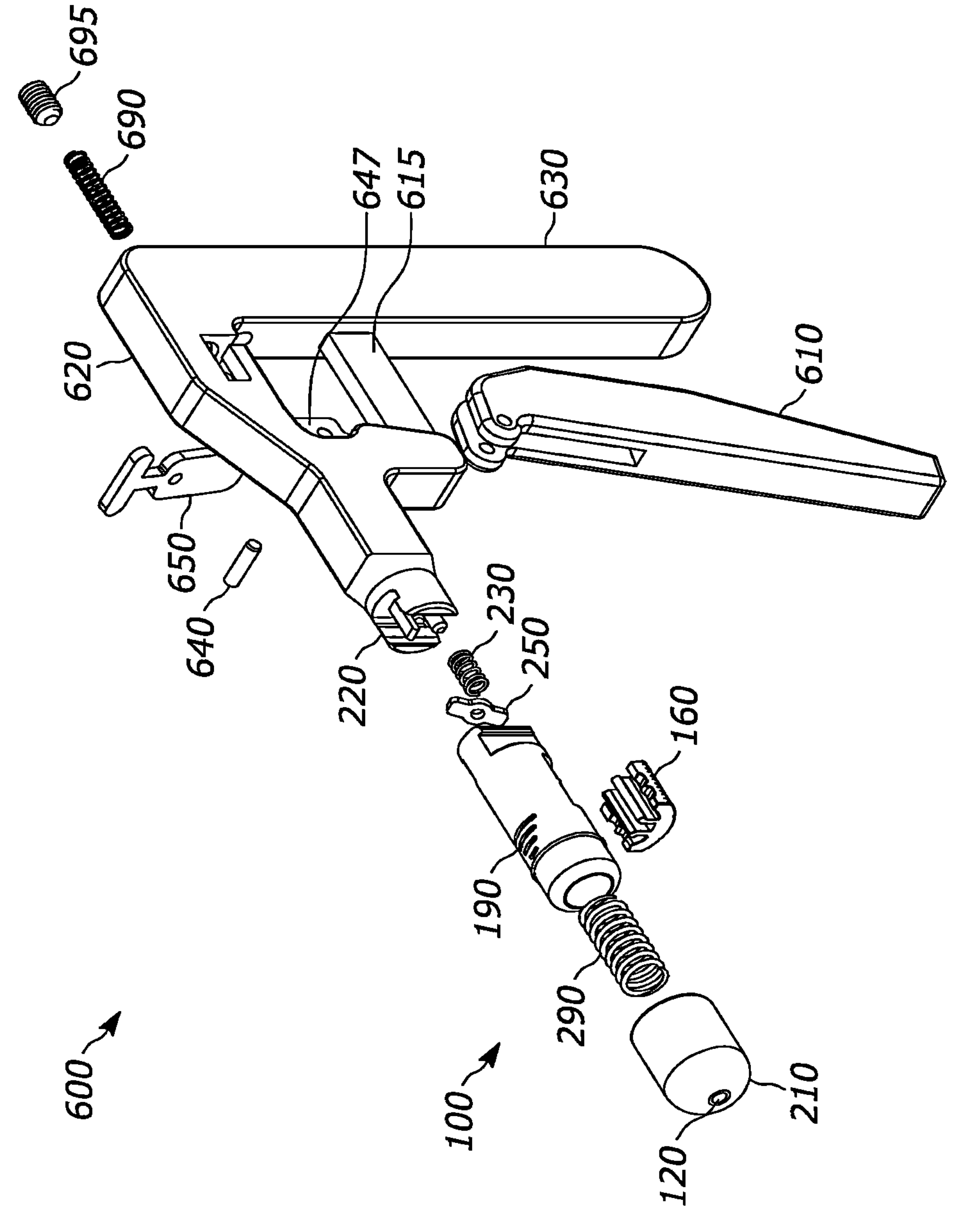
FIG. 7C shows an exploded view of the second example embodiment of the hand-held advancement mechanism consistent with present principles.
Figure 7D:
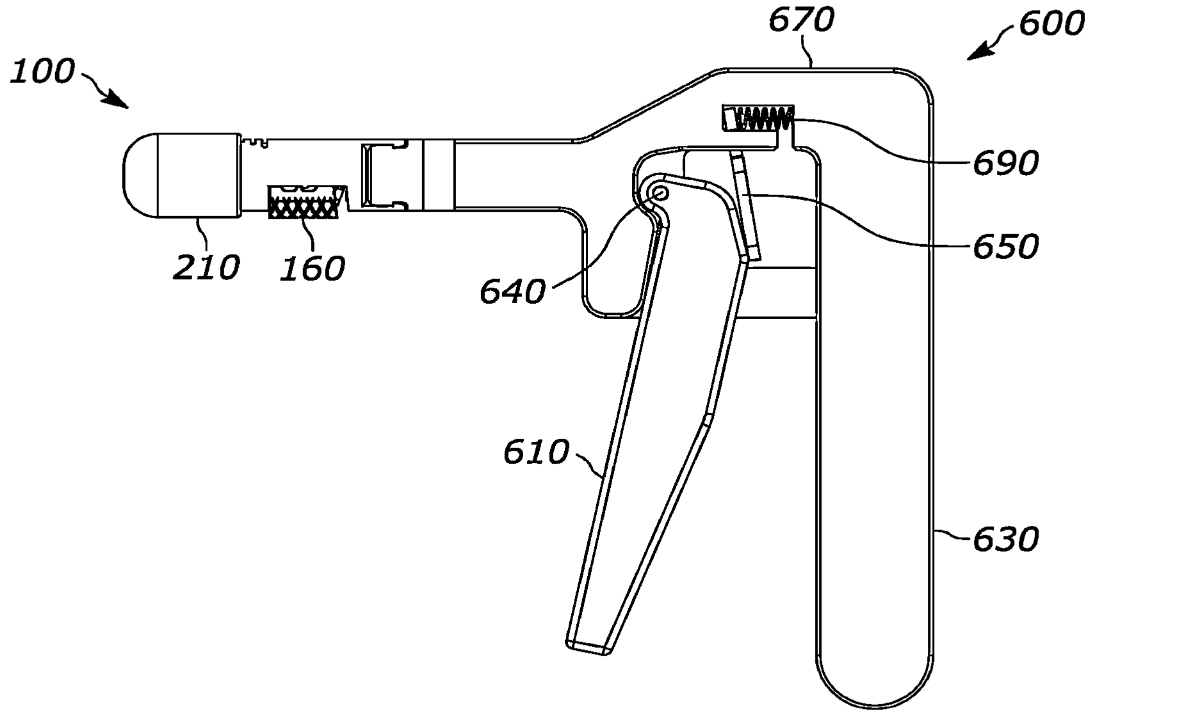
FIG. 7D shows an orthogonal side view of the second example embodiment of the hand-held advancement mechanism consistent with present principles.
Figure 7E:
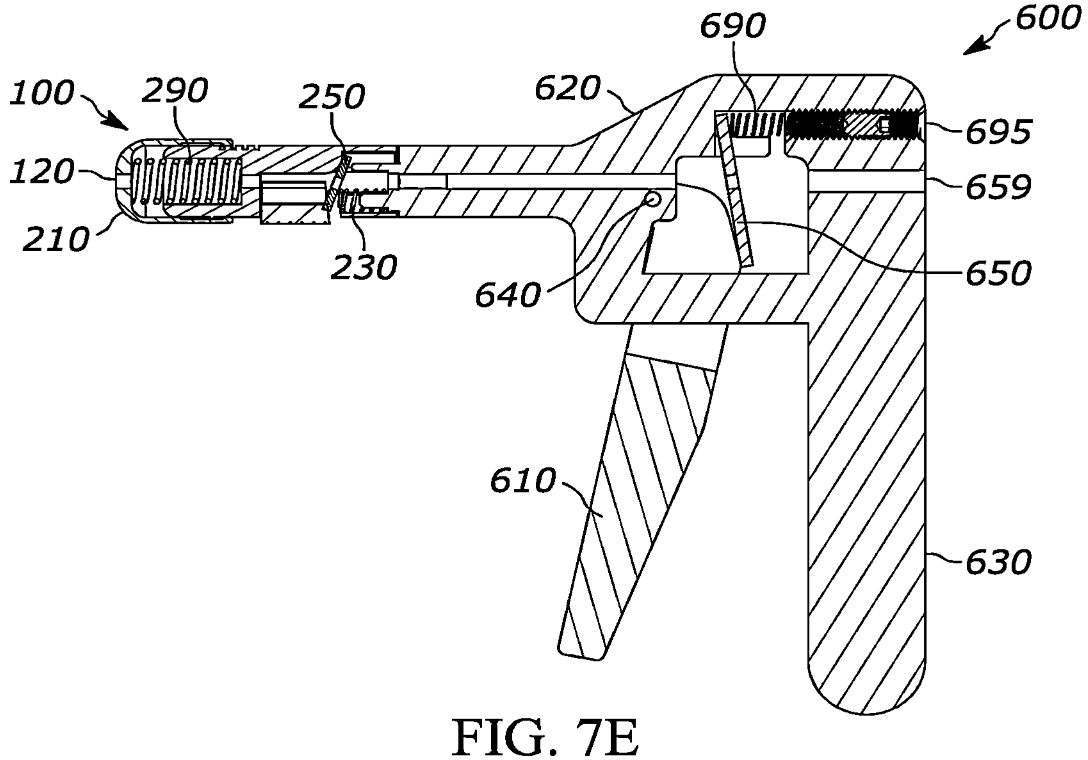
FIG. 7E shows a cross-sectional view of the second example embodiment of the hand-held advancement mechanism consistent with present principles.

Turning now to FIGS. 7A-E, another example is shown where the mechanism 600 is made integral with the rear cap 220 and/or body 200 of the device 100 so that the whole unit 100/600 may be advanced along a surgical guide wire and then withdrawn when desired. FIG. 7A is a front isometric view, FIG. 7B is a rear isometric view, FIG. 7C is an exploded view, FIG. 7D is a side orthogonal view, and FIG. 7E is a side cross-sectional view. The devices 100, 600 according to FIGS. 7A-E may therefore be the same as other example embodiments above save for the mechanism 600 and one or more portions of the housing 105 being made integral with each other (instead of, in contrast, the device 100 and mechanism 600 being independent of each other per FIGS. 6A-6K).

Figure 8A:
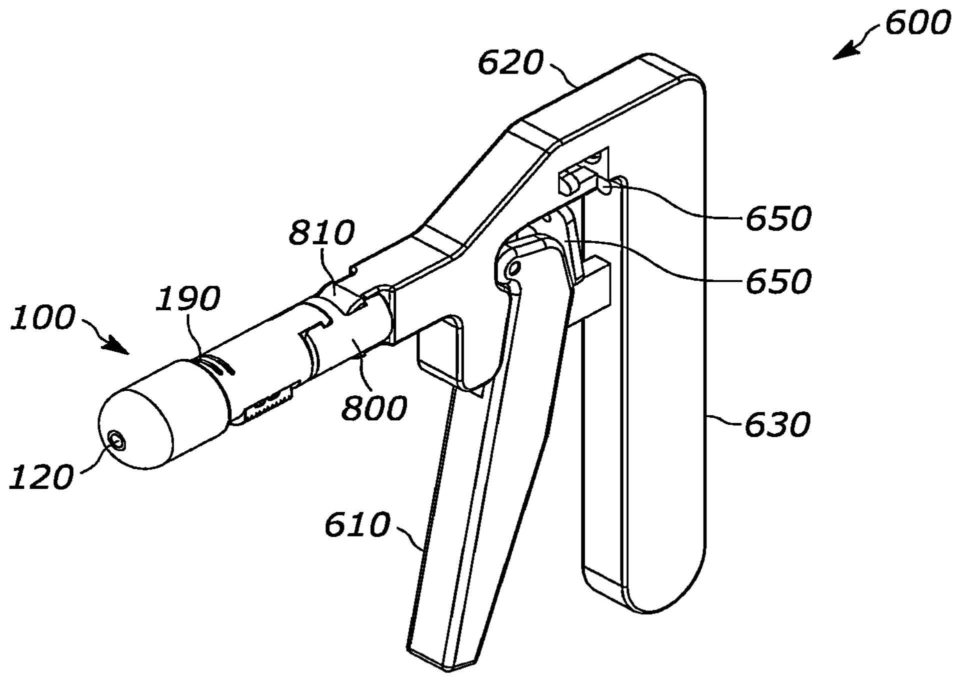
FIG. 8A shows a front isometric view a third example embodiment of the hand-held advancement mechanism consistent with present principles.
Figure 8B:
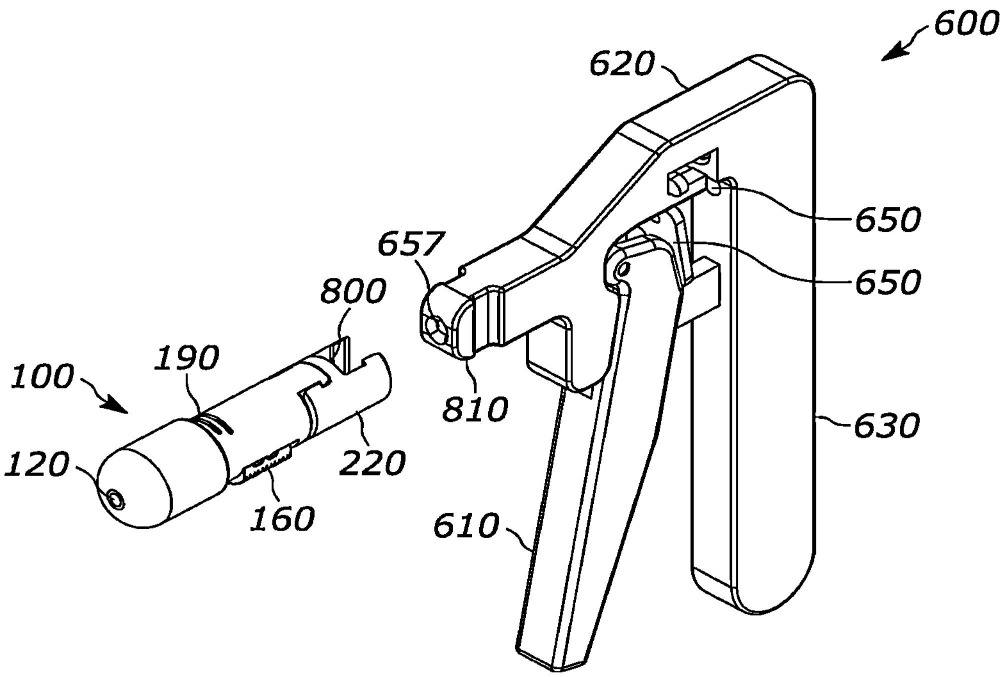
FIG. 8B shows an exploded view of the third example embodiment of the hand-held advancement mechanism consistent with present principles.
Figure 8C:
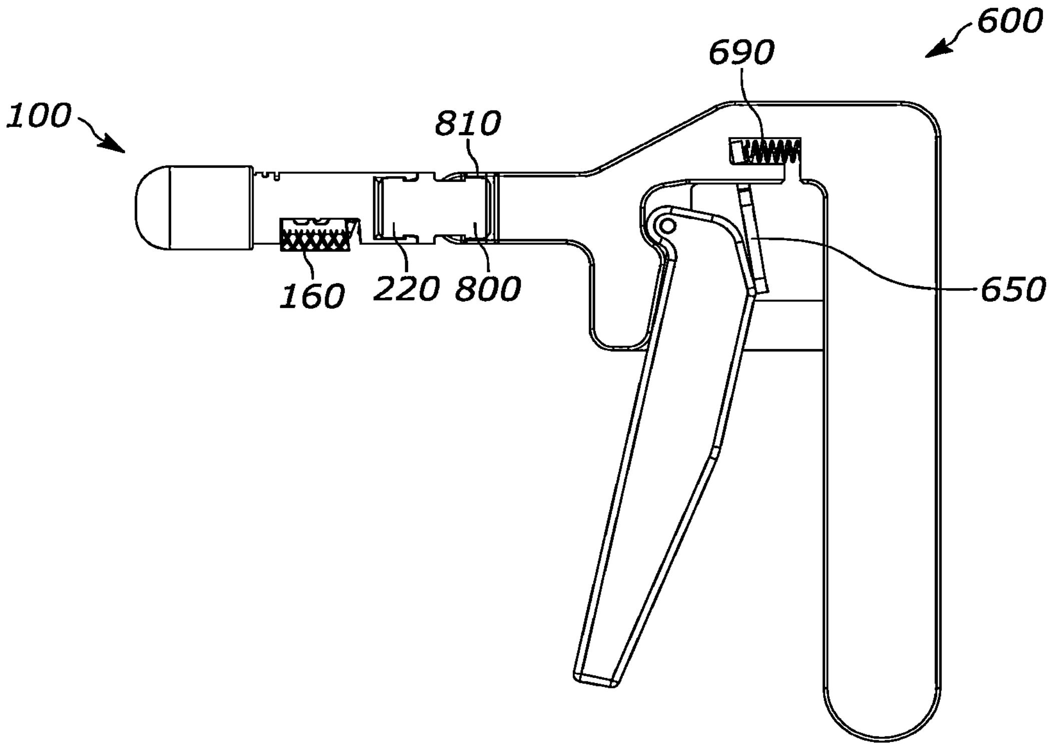
FIGS. 8C-8D show orthogonal views of the third example embodiment of the hand-held advancement mechanism consistent with present principles.
Figure 8D:
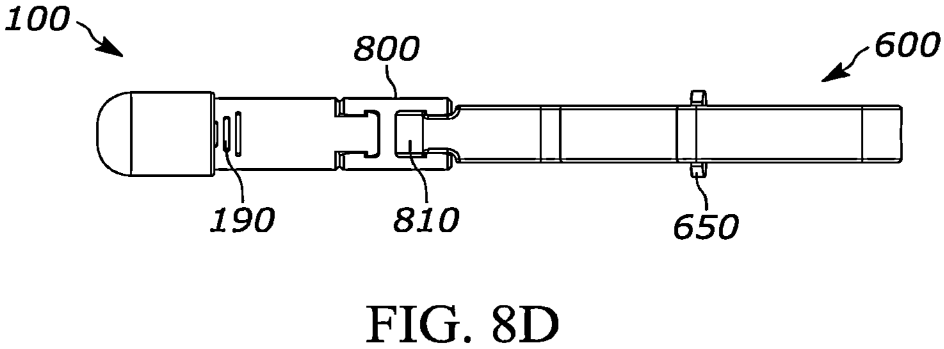

Moving on to FIGS. 8A-8D, another example is shown where the mechanism 600 is attachable and detachable from the rear cap 220 and/or body 200 by hand in the surgical environment, but where the whole unit 100/600 may still be advanced together along the surgical guide wire. Then when the device 100 is at a desired position, the mechanism 600 may be detached from the device 100 while both are still on the wire so the mechanism 600 may then be withdrawn and the device 100 left in place on the wire. FIG. 8A is a front isometric view, FIG. 8B is a front isometric view but in an exploded state to show separation of the couplable components, FIG. 8C is a side orthogonal view, and FIG. 8D is a top orthogonal view. The devices 100, 600 according to FIGS. 8A-8D may therefore be the same as other example embodiments above save for the mechanism 600 and one or more portions of the housing 105 being attachable and detachable from each other on the fly.

For attachment and detachment, a distal portion of the rear cap 220 may have a female mating element 800 configured to engage a male mating element 810 on a distal front end portion of the mechanism 600 via snap fit. This in turn allows the device 100 to be pulled off/detached from the mechanism 600 and reattached/pushed back on to the mechanism 600 on the fly in the surgical environment, using only the physician's hands.

Figure 9A:
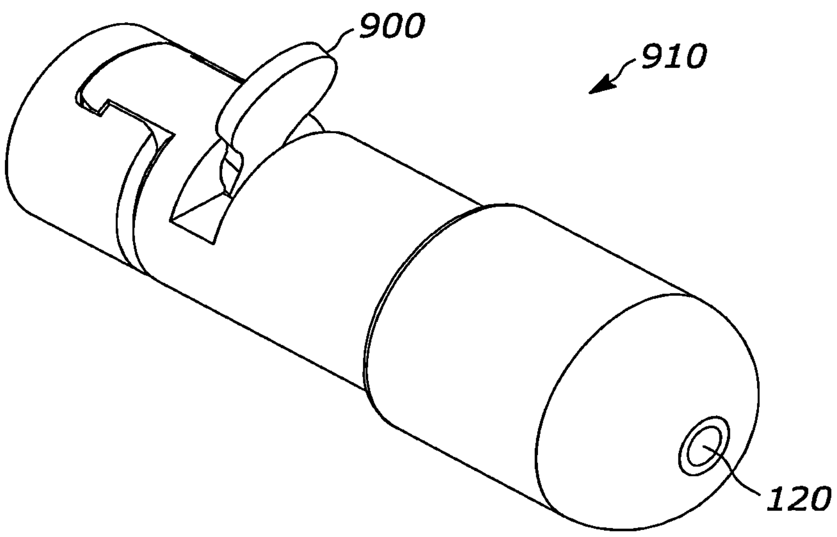
FIG. 9A shows a front isometric view of a second example embodiment of a medical device similar to the device of FIGS. 1A-3 consistent with present principles.
Figure 9B:
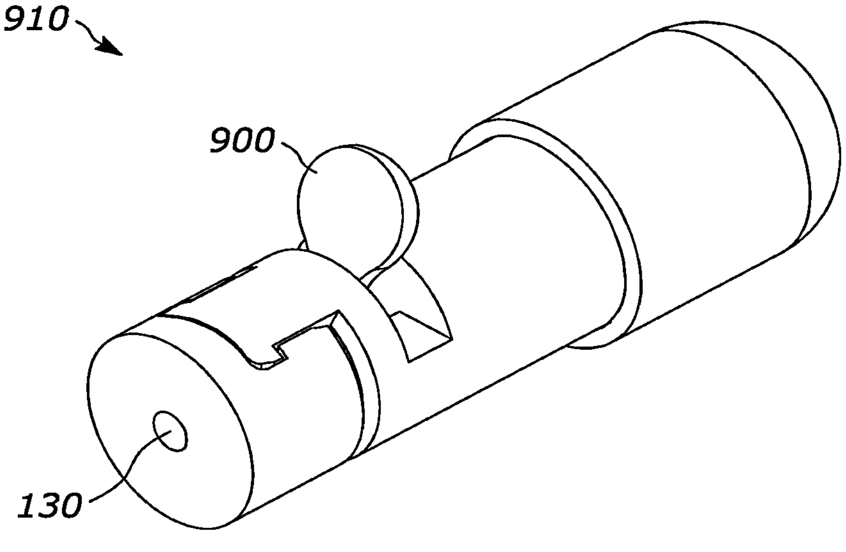
FIG. 9B shows a rear isometric view of the second example embodiment of the medical device consistent with present principles.
Figure 9C:
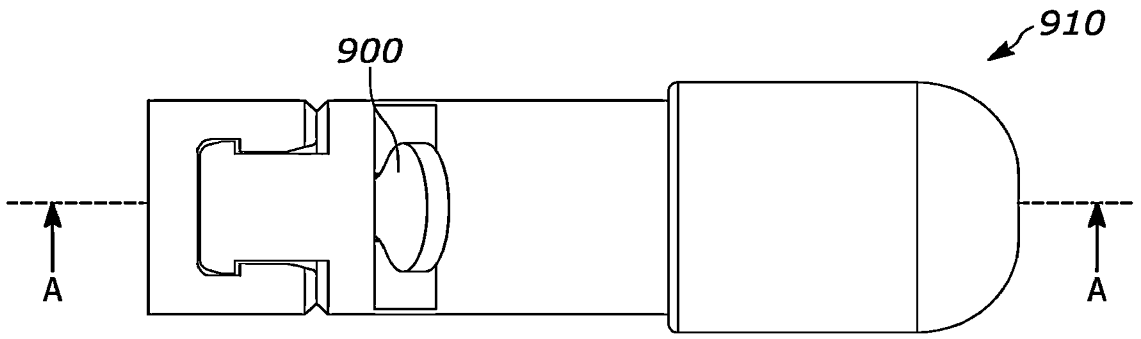
FIGS. 9C-9G show various orthogonal views of the second example embodiment of the medical device consistent with present principles.
Figure 9D:
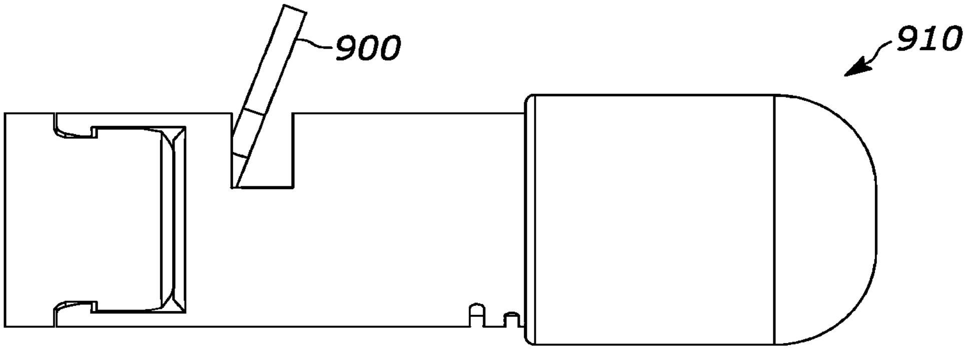
Figure 9E:
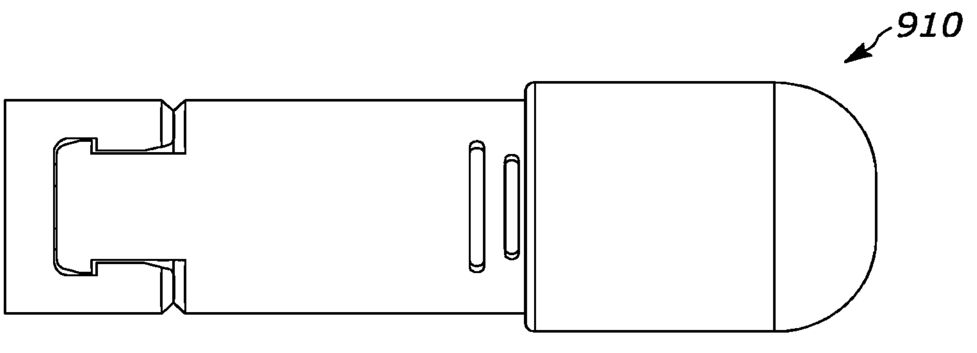
Figure 9F:
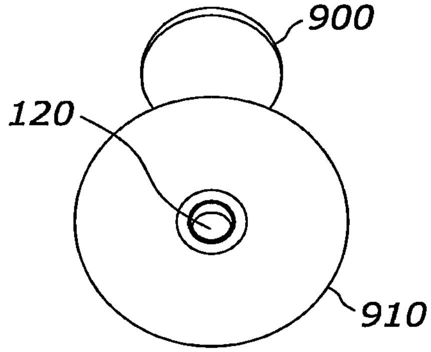
Figure 9G:
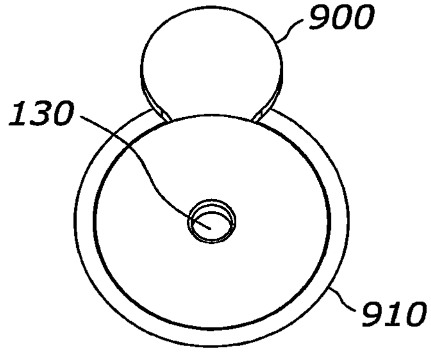
Figure 9H:
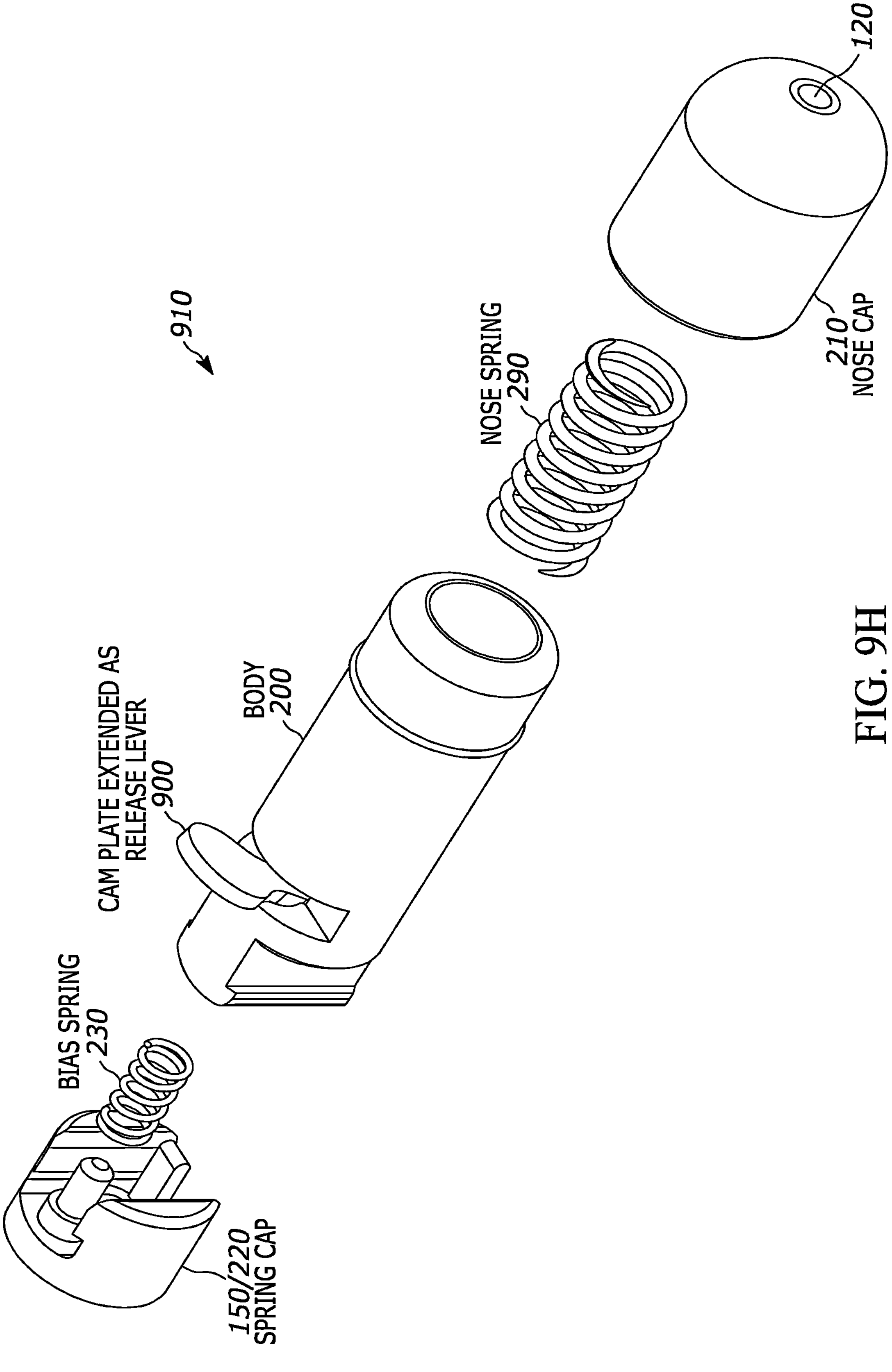
FIG. 9H shows an exploded view of the second example embodiment of the medical device consistent with present principles.
Figure 9I:
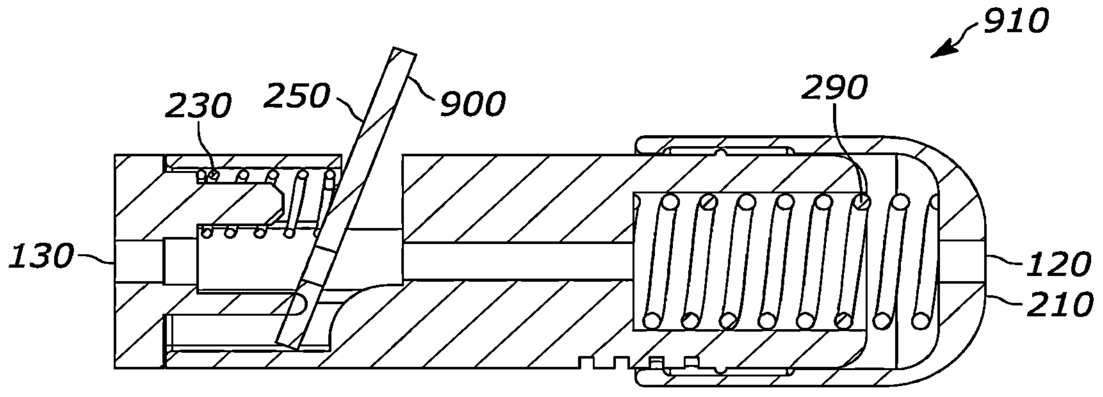
FIG. 9I shows a side cross-sectional view of the second example embodiment of the medical device consistent with present principles.

Now in reference to FIGS. 9A-9I, these figures show another example medical device 910 consistent with present principles. FIG. 9A is a front isometric view, FIG. 9B is a rear isometric view, FIG. 9C is a top orthogonal view, FIG. 9D is a side orthogonal view, FIG. 9E is a bottom orthogonal view, FIG. 9F is a front orthogonal view, FIG. 9G is a rear orthogonal view, FIG. 9H is an exploded view, and FIG. 9I is a cross-sectional view. The device 910 per these figures may be the same as the device 100 described above, save for the following differences.

Specifically, rather than a slider release mechanism 160 as described above, the release mechanism per this example implementation may include a lever/tab 900 coupled to the plate 250. For example, the lever 900 may be made integral with the plate 250 and, as such, may be made of the same material as the plate itself. The lever 900 may be manipulable to move the plate 250 about the fulcrum 300 to counteract the spring bias from the spring 230 and permit withdrawal of the surgical guide wire 115 from the third aperture 260 through the first aperture 120. As shown, the distal top portion of the lever may be circular, though other shapes may also be used. Thus, a physician may pull the lever back away from the nose cap 210 according to the longitudinal axis 110 to release the binding action the aperture 260 creates on the wire 115 by aligning the third plane of the plate 250 closer to vertical/perpendicular to the longitudinal axis 110, freeing up the wire 115 to withdraw the device 910 from the wire 115.

Beyond the slider 160 and lever 900, as another example release mechanism may be an element that connects to the body 200 at a pivot point with an axis of rotation perpendicular to the longitudinal axis 110 of the device 100 to rotate up and down the housing. When rotated toward the plate 250 the element slides against and pushes on the plate 250 causing the plate 250 to rotate. This motion will release the binding action the aperture 260 creates on the wire 115 by aligning the third plane of the plate 250 closer to vertical/perpendicular to the longitudinal axis 110, freeing up the wire 115 to withdraw the device 100 from the wire 115.

Figure 10A:
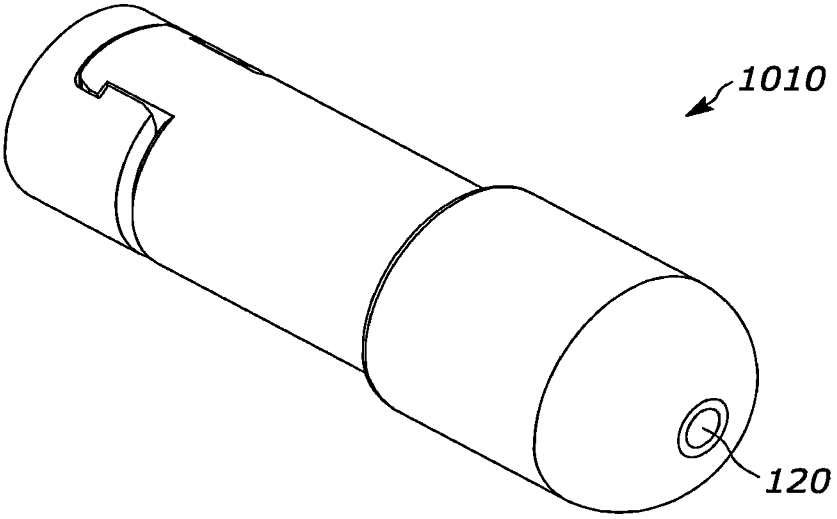
FIG. 10A shows a front isometric view of a third example embodiment of a medical device similar to the device of FIGS. 1A-3 consistent with present principles.
Figure 10B:
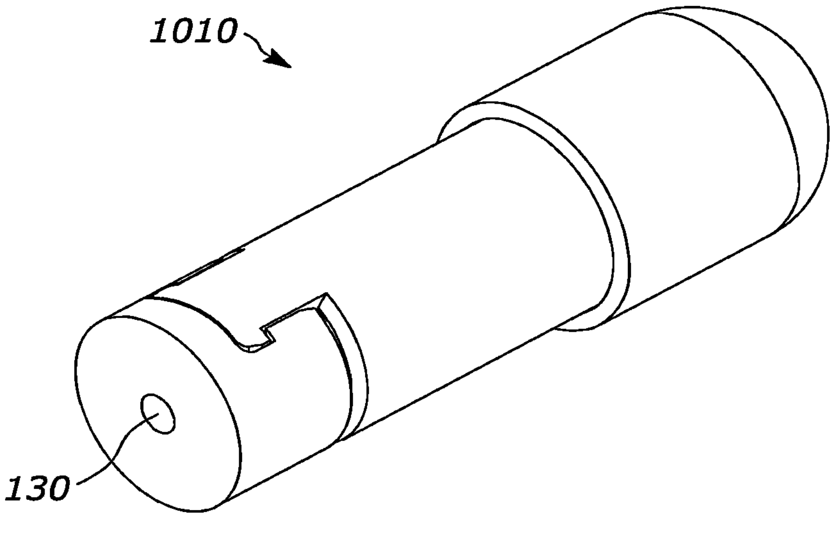
FIG. 10B shows a rear isometric view of the third example embodiment of the medical device consistent with present principles.
Figure 10C:
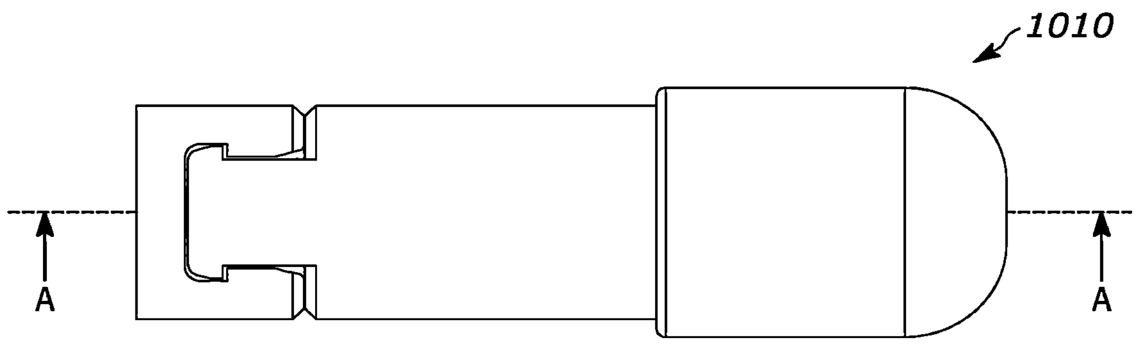
FIGS. 10C-10G show various orthogonal views of the third example embodiment of the medical device consistent with present principles.
Figure 10D:
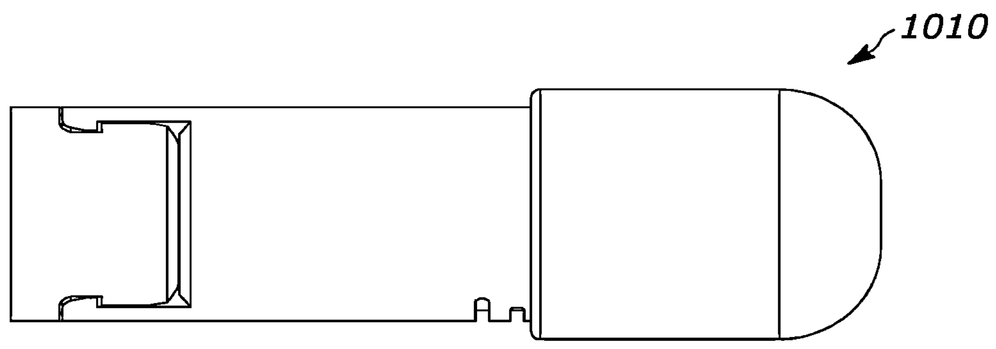
Figure 10E:
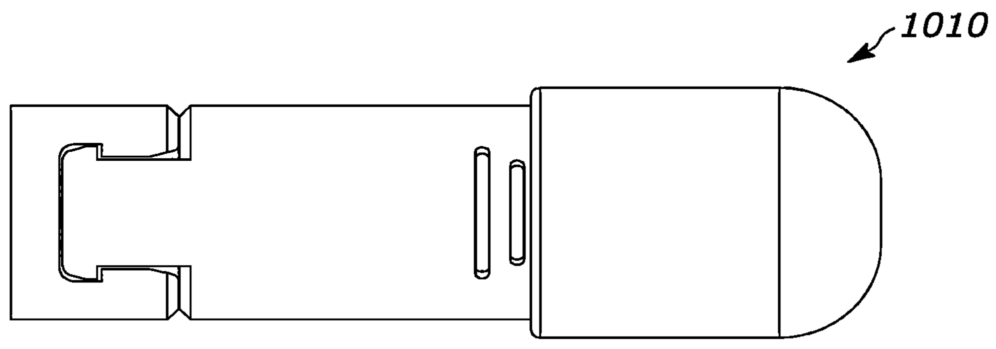
Figure 10F:
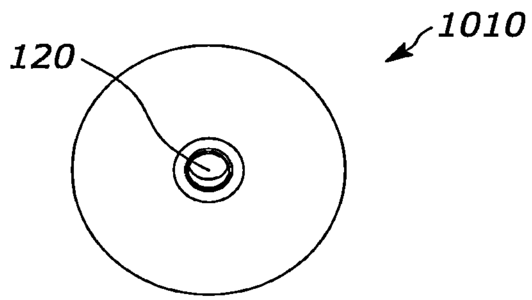
Figure 10G:
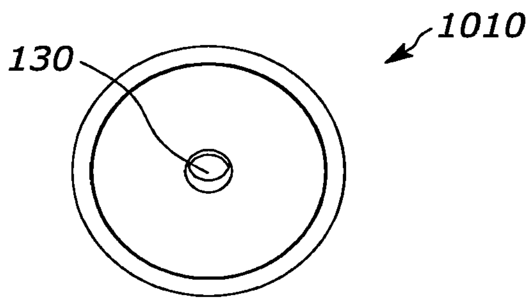
Figure 10H:
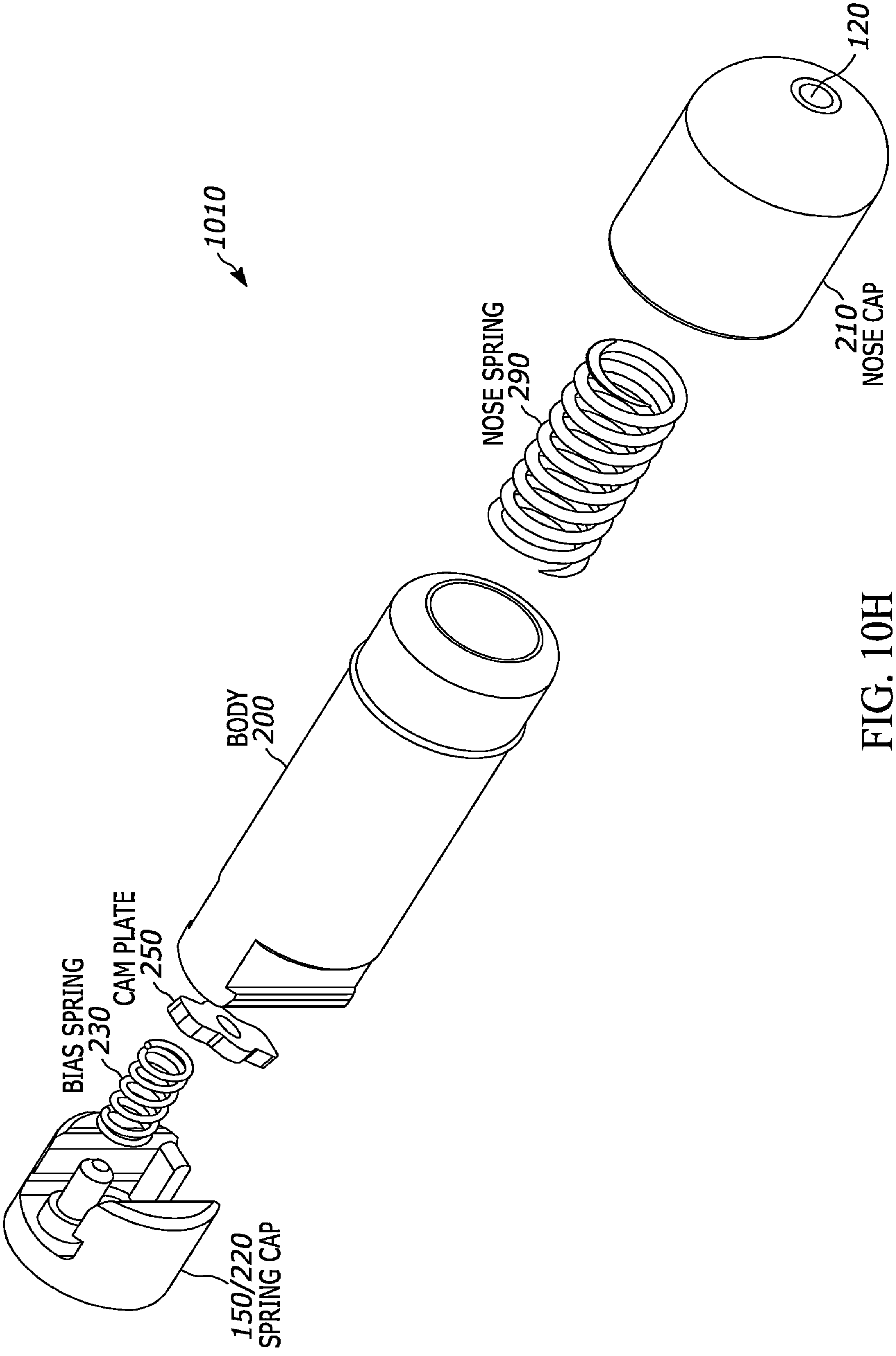
FIG. 10H shows an exploded view of the third example embodiment of the medical device consistent with present principles.
Figure 10I:
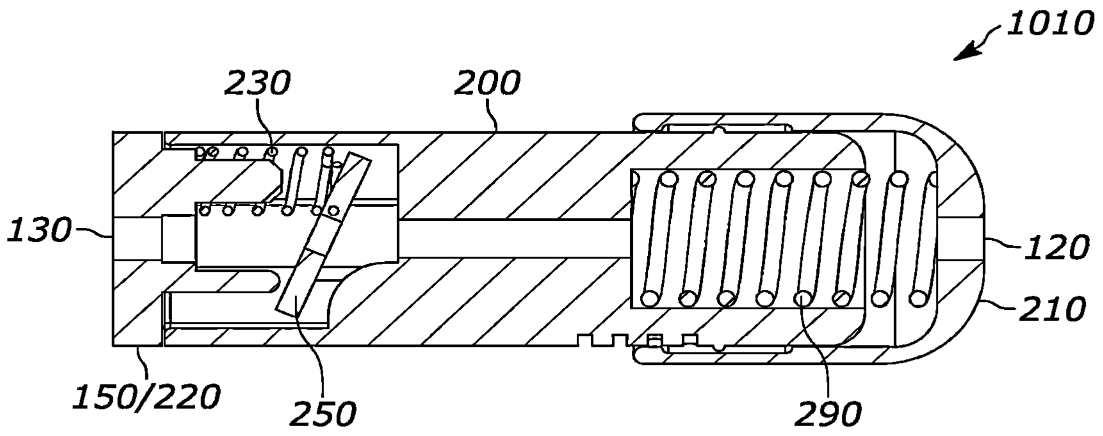
FIG. 10I shows a side cross-sectional view of the third example embodiment of the medical device consistent with present principles.

Continuing the detailed description in reference to FIGS. 10A-10I, these figures show another example device 1010. FIG. 10A is a front isometric view, FIG. 10B is a rear isometric view, FIG. 10C is a top orthogonal view, FIG. 10D is a side orthogonal view, FIG. 10E is a bottom orthogonal view, FIG. 10F is a front orthogonal view, FIG. 10G is a rear orthogonal view, FIG. 10H is an exploded view, and FIG. 10I is a cross-sectional view. The device 1010 per these figures may be the same as the device 100 described above, save for the following differences.

Specifically, no release mechanism may be included on the device 1010 per this example implementation. Instead, the physician may simply remove the wire 115 with the device 1010 still attached to it when a desired bone and/or plate alignment is obtained so that permanent, larger holes may then be bored into the bone. Or the wire may simply be cut in front of the device 1010 and proximal to the patient to remove the device 1010.

Figure 11A:
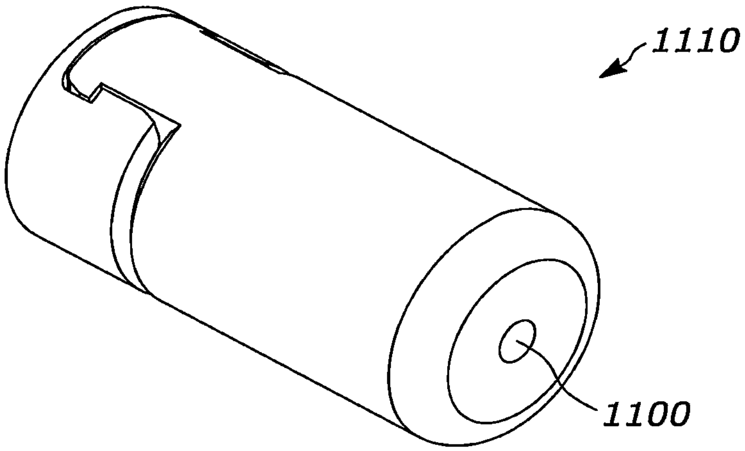
FIG. 11A shows a front isometric view of a fourth example embodiment of a medical device similar to the device of FIGS. 1A-3 consistent with present principles.
Figure 11B:
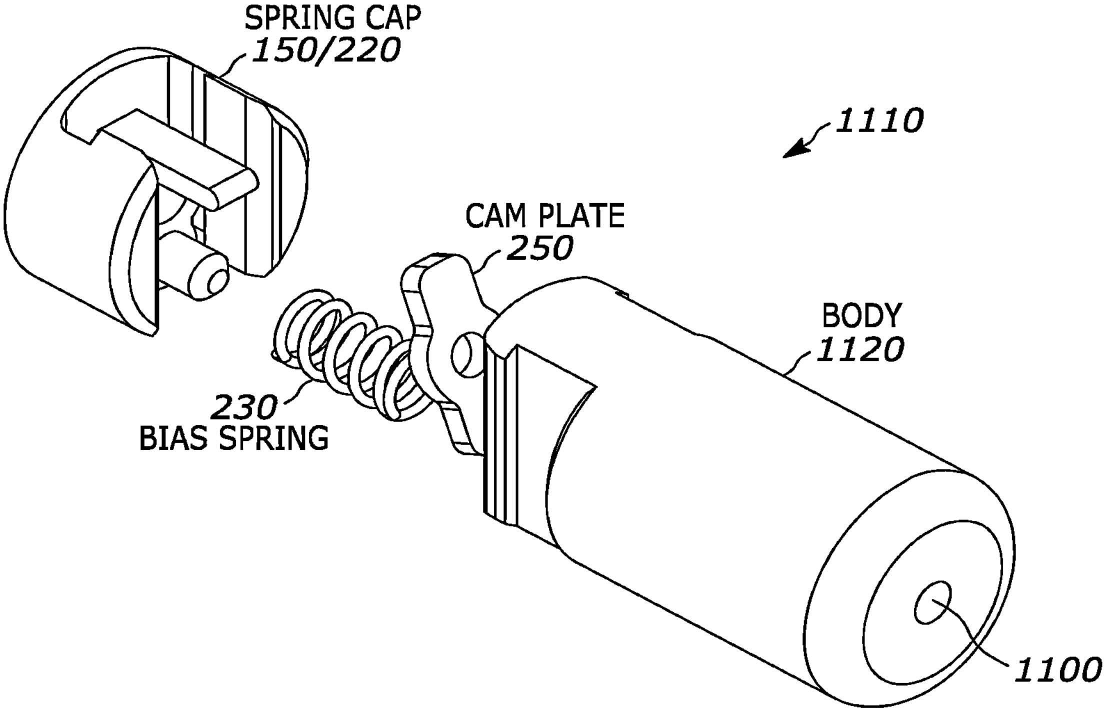
FIG. 11B shows an exploded view of the fourth example embodiment of the medical device consistent with present principles.
Figure 11C:
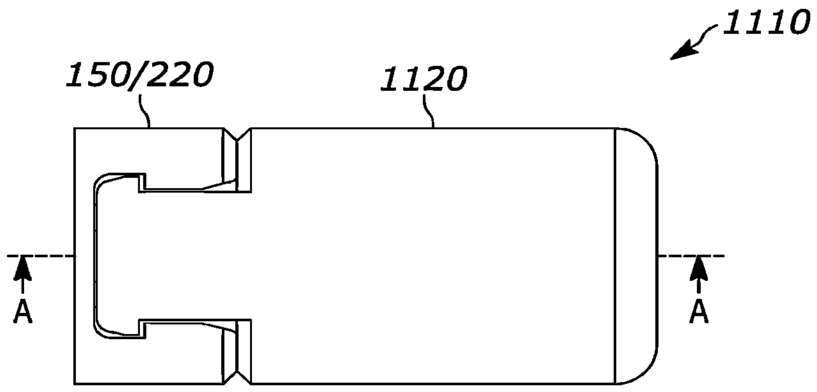
FIG. 11C shows an orthogonal side view of the fourth example embodiment of the medical device consistent with present principles.
Figure 11D:
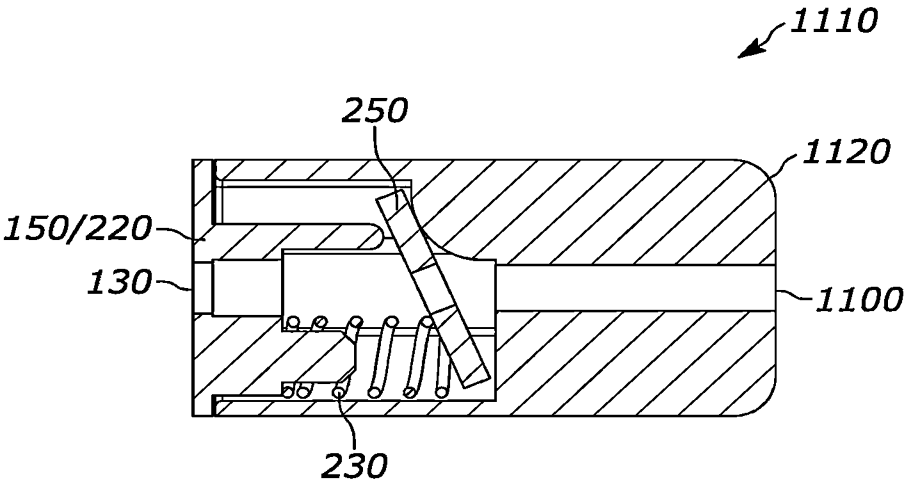
FIG. 11D shows a side cross-sectional view of the fourth example embodiment of the medical device consistent with present principles.

Now in reference to FIGS. 11A-11D, these figures show another example device 1110. FIG. 11A is a front isometric view, FIG. 11B is an exploded view, FIG. 11C is a side orthogonal view, and FIG. 11D is a cross-sectional view. The device 1110 per these figures may be the same as the device 100 described above, save for the following differences.

Specifically, no telescoping members at the front are included on the device 1110, nor is any release mechanism. Rather, a front aperture 1100 is included and may be similar to the aperture 120 except for being made integral with the rigid body 1120 of the device's housing. Note here that the front of the device 1110 may be flat as shown, or rounded in other examples.

Figure 12:
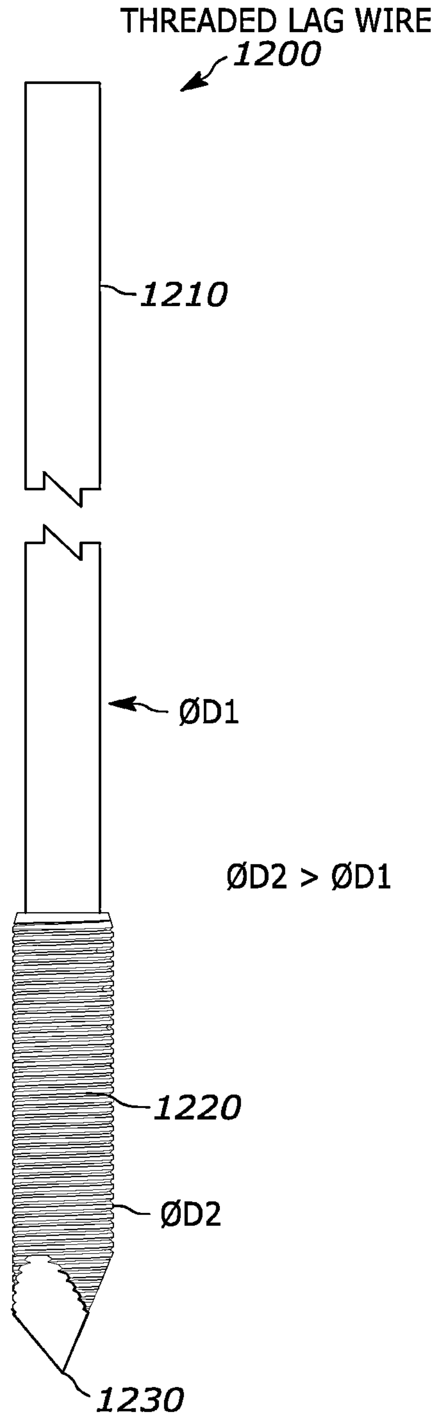
FIG. 12 shows an innovative guide wire that may be used consistent with present principles.

Moving on to FIG. 12, this figure shows an innovative threaded lag wire 1200 that may be used with the devices 100, 600, etc. described above. As shown in FIG. 12, the wire 1200 may include a first segment 1210 that may be cut by a physician to a desired length. The segment has a first diameter that is less than a second diameter of a threaded second segment 1220 of the wire 1200. Also note that the segment 1220 has a pointed distal tip 1230.

Thus, the threads on the segment 1220 may be extended through provisional holes in the patient's bone to capture a far piece of the bones and/or plates that are being aligned together. The threads and larger diameter of the segment 1220 may thus help create compression force on one end of the aligned bones/plates, while the devices 100/600 create compression force on the other end of the aligned bones/plates. In some examples, ridges that circumscribe the outside of the segment 1220 in respective planes perpendicular to the longitudinal axis of the wire 1200 may be used in lieu of screw-type threads that extend down the segment 1220 for even greater bone purchase/engagement.

Figure 13:
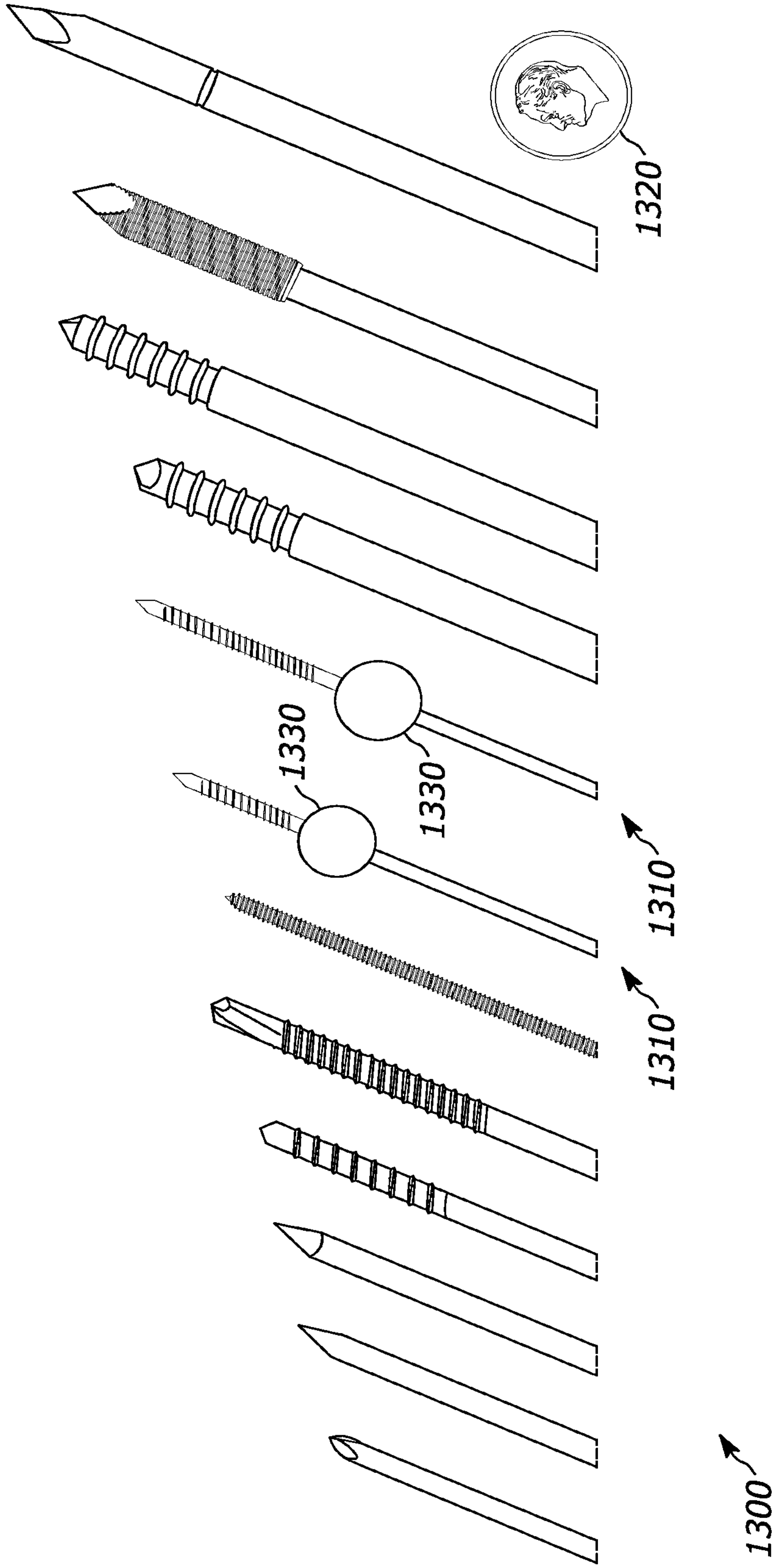
FIG. 13 shows other example guide wires that may be used consistent with present principles.

Turning to FIG. 13, additional guide wire examples 1300 are shown that may be used consistent with present principles. Among these guide wire examples are olive wires 1310. The diameters of these flexible wires 1300 (equivalently, rigid guide pins) may be appreciated relative to the dime 1320 shown. Also note that some of the wires 1300 may be threaded while others are not. Also note that the olive wires 1310 may be used, where the olives 1330 may provide compression force at one end of the bone alignment while the device 100 may provide compression force at the other end of the bone alignment.

Figure 14:
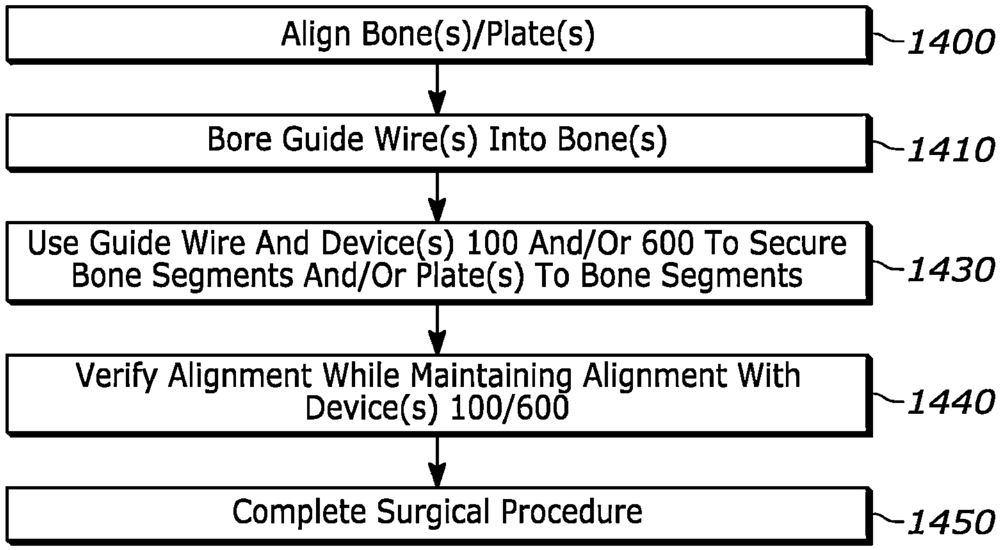
FIG. 14 shows an example method in flow chart format for surgically using a medical device consistent with present principles.

Now in reference to FIG. 14, an example method is demonstrated in flow chart format for surgically using a medical device (such as the device 100) consistent with present principles. Beginning at step 1400, the method includes initially aligning various patient bones and/or surgical plates for fixation together consistent with present principles. The method then moves to step 1410 where guide wire(s) (provisional) are bored through the bone(s) according to the desired alignment.

Then at step 1430, the guide wire and the devices 100/600 may be used to provide compression force to secure the bone segments and/or to secure one or more plates to the bone segments, maintaining the alignment. For example, a free end of the wire may be fed through the first aperture 120, then through the aperture 260, and then through the aperture 130. The device 100 may then continue to be advanced/slid along the wire as desired using the mechanism 600 (or by hand) until the device 100 is compressed against one side of the aligned bone structure. Yet owing to the oblique angle of the aperture 260 relative to the longitudinal axis of the device 100 as described above, the device 100 cannot be withdrawn or unintentionally slide off the opposite way along the wire save for using one of the release mechanisms described above (e.g., slider 160 and/or lever 900).

Then at step 1440 the physician may verify the intended alignment of the bones and/or plates with the devices 100/600 holding the alignment in place (e.g., on one side of the aligned bones while the segment 1220 of the wire 1200 helps maintain the alignment on the other side of the aligned bones/plates). The process may then flow to step 1450 where the devices 100/600 and/or guide wire may be removed from the patient. Also at step 1450, the surgical procedure may be completed with bone/plate alignment verified by drilling permanent holes in the bone(s) and performing permanent fracture reduction. This last step might occur, for example, after one or more alignment adjustments are performed as desired, using the devices 100/600 in the process.

It may thus be appreciated according to FIG. 14 that the medical device and wire may be used to maintain alignment of a first bone with another object (e.g., second bone and/or plate) during the surgical procedure.

Figure 15:
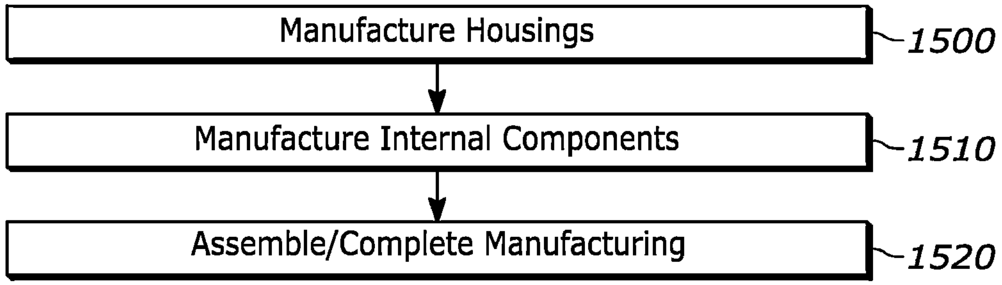
FIG. 15 shows an example method in flow chart format for manufacturing a medical device consistent with present principles.

FIG. 15 shows an example method in flow chart format for manufacturing a medical device, such as the device 100 and/or mechanism 600, consistent with present principles. Beginning at step 1500, the housing(s) may be manufactured, such as through injection molding, three-dimensional (3D) printing, computer numerical control (CNC) manufacturing, and/or other methods. Thereafter, step 1510 may be performed where the internal components of the device(s) may be manufactured using similar methods. Then at step 1520 manufacturing may be completed, such as through assembling all the parts together for shipping, vending, providing, etc.

Figure 16:
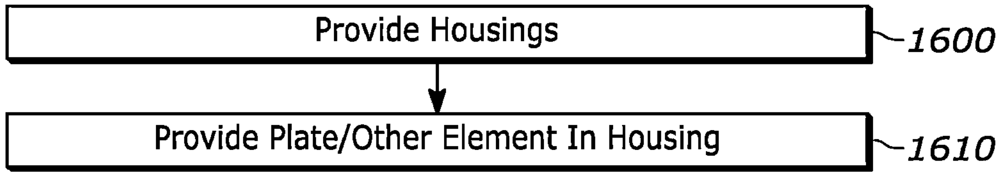
FIG. 16 shows an example method in flow chart for providing a medical device consistent with present principles.

Now in reference to FIG. 16, this figure shows an example method in flow chart for providing a medical device consistent with present principles. Thus, note that the process flow of FIG. 16 may be used for vending or otherwise providing the medical device through the channels of commerce and ultimately to a medical professional.

Thus, the method includes, at step 1600, providing a housing with an elongated body. The housing defines a longitudinal axis. The housing includes a first end portion and a second end portion. The first end portion includes a first aperture. The second end portion includes a second aperture. The first aperture has a first height and first width establishing a first plane, and the second aperture has a second height and a second width establishing a second plane.

The method of FIG. 16 also includes, at step 1610, providing a first element disposed within the housing (e.g., plate or other assembly with an aperture like the third aperture 260). The first element therefore includes the third aperture. The third aperture has a third height and a third width establishing a third plane. The third plane is oblique with respect to the longitudinal axis while the first element is under bias from a second element in the housing. The first, second, and third apertures are at least partially aligned for a wire to concurrently extend through the first, second, and third apertures while the first element is under bias from the second element. The bias is toward the first end portion. The second element configured in the housing to impose the bias on the first element at a first area of the first element to help maintain the oblique angle of the third plane with respect to the longitudinal axis and to impede withdrawal of the wire from the third aperture toward the first aperture while the wire extends through the third aperture. A second area of the first element is configured within the housing to rest against a fulcrum within the housing. The first element is configured within the housing to rotate during advancement of the wire through the third aperture from the direction of the first aperture due to friction force during the advancement between the wire and one or more first element portions around the third aperture.

Continuing the detailed description in reference to FIGS. 17-20, these figures show example use cases for the devices 100/600 consistent with present principles to create axial pressure on bones and/or plates along the axis of the surgical guide wire itself.

Figure 17:
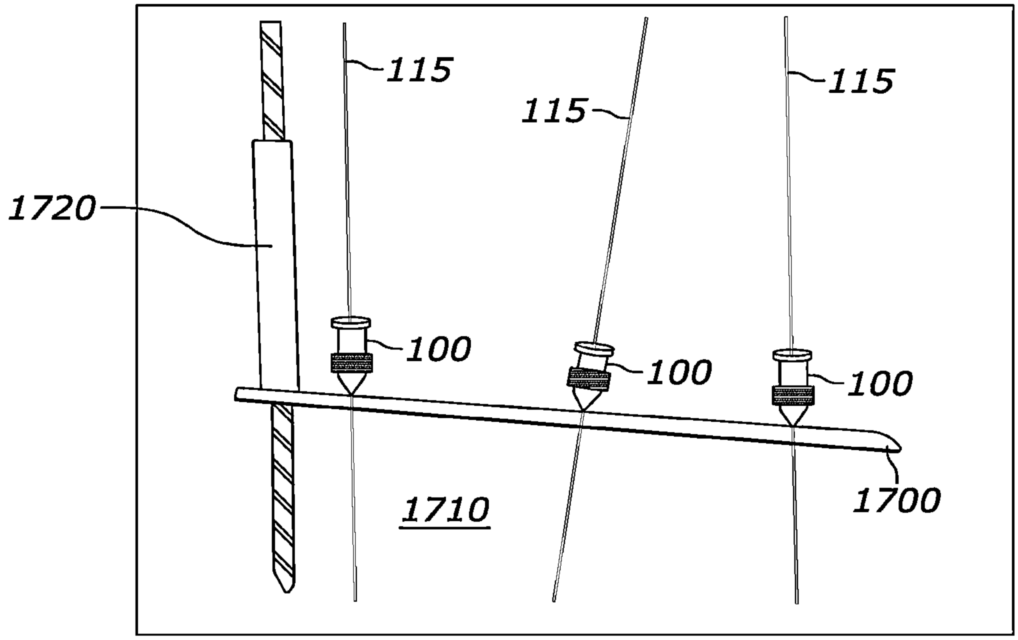
FIGS. 17-20 show various example use cases of the medical devices disclosed herein consistent with present principles.

Beginning first with FIG. 17, respective devices 100 are shown as advanced along respective wires 115 to compress against a surgical plate 1700 that itself is positioned up against a patient's bone 1710. If desired, a surgical tool 1720 may also be positioned against the plate 1700 to help maintain alignment. Thus, according to this example the devices 100 may provide a relatively slight one-sided axial reduction force, no additional surgical clamp being used, once slid down the wire 115 to keep the plate from moving during installation/permanent fixation.

Figure 18:
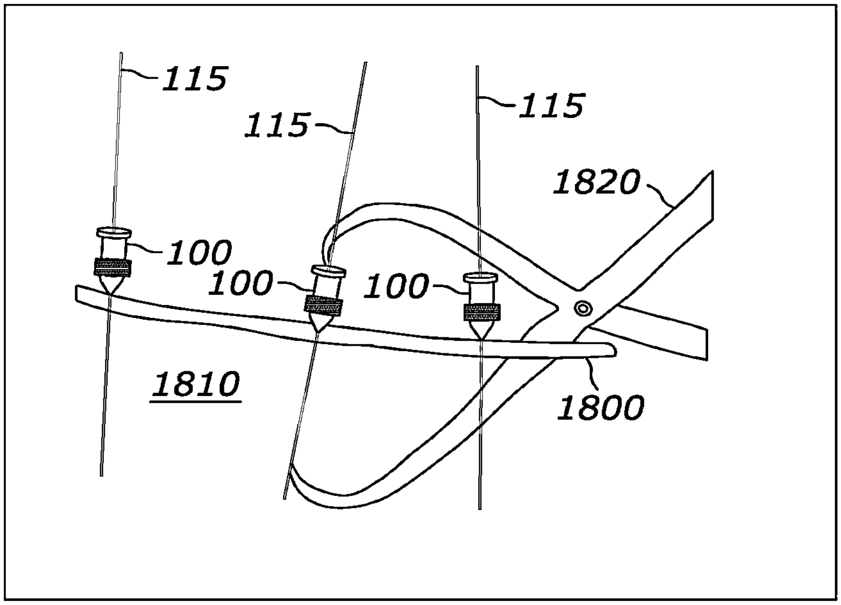

FIG. 18 shows another example. Here, respective devices 100 are again shown as advanced along respective wires 115 to compress against a surgical plate 1800 that itself is positioned up against a patient's bone 1810. A surgical clamp 1820 is also used to compress a respective device 100 on one side of the aligned bone(s)/plate with the other side of the aligned bone(s)/plate. This provides relatively significant axial reduction force to reduce the plate 1800 to the bone 1810 with the clamp 1820.

Figure 19:
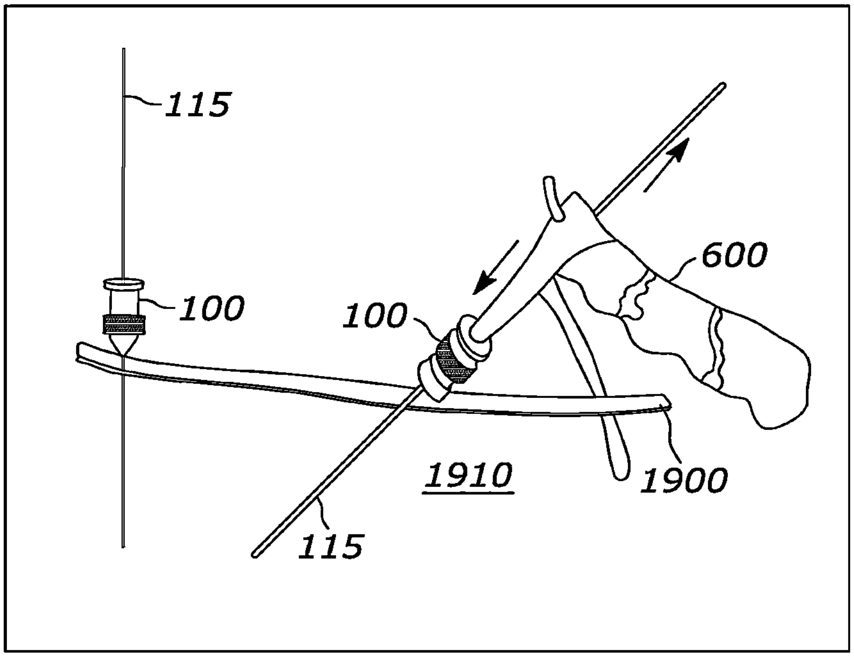

Turning to FIG. 19, yet another example is shown. Here, respective devices 100 are again shown as advanced along respective wires 115 to compress against a surgical plate 1900 that itself is positioned up against a patient's bone 1910. Note that one device 100 is shown being used by itself, while another device 100 is shown as advanced along the respective guide wire 115 using the mechanism 600 before the mechanism 600 is withdrawn from the wire 115 (leaving the device 100 advanced by the mechanism 600 in place and locked along the wire 115 for compression against the plate 1900). This example therefore demonstrates a higher one-sided axial reduction force (no clamp being used) to reduce the plate 1900 to the bone 1910, and/or to capture and temporarily reduce a bone fragment through the plate 1900.

Figure 20:
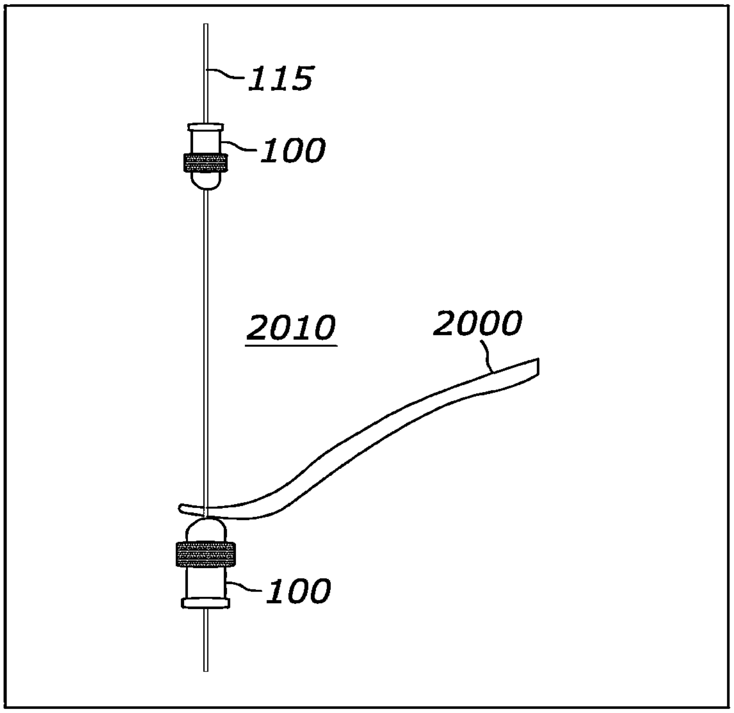

FIG. 20 shows still another example. Here, respective devices 100 are shown facing each other as advanced from opposing sides of a same wire 115, with one of the devices 100 advanced to compress a plate 2000 to one side of a bone structure 2010 and the other device 100 advanced on the other side of the bone structure to compress against an external portion of the structure 2010 itself. This allows for relatively significant axial reduction force to reduce the plate 2000 to the bone(s) 2010 with two sliding pill/tack devices 100.

Moving on from FIG. 20, note that in some specific examples a kit including one or more of the devices/mechanisms disclosed above (and/or sub-components of those devices) may be manufactured, vended/provided, and/or used during a fracture reduction procedure or other type of surgical procedure consistent with present principles. Surgical alignment wires of one or more types disclosed herein may also be provided as part of the kit. The surgeon may thus decide on the fly which wire/device combination from the kit to use, depending on whatever circumstances the surgeon might encounter during surgery.

Components included in one embodiment can be used in other embodiments in any appropriate combination. For example, any of the various components described herein and/or depicted in the Figures may be combined, interchanged, or excluded from other embodiments.

The term “a” or “an” in reference to an entity refers to one or more of that entity. As such, the terms “a” or “an”, “one or more”, and “at least one” can be used interchangeably herein.

“A system having at least one of A, B, and C” (likewise “a system having at least one of A, B, or C” and “a system having at least one of A, B, C”) includes systems that have A alone, B alone, C alone, A and B together, A and C together, B and C together, and/or A, B, and C together, etc.

It is to be understood that whilst present principals have been described with reference to some example embodiments, these are not intended to be limiting, and that various alternative arrangements may be used to implement the subject matter claimed herein. Accordingly, while particular techniques and devices are herein shown and described in detail, it is to be understood that the subject matter which is encompassed by the present application is limited only by the claims.

What is claimed is:

1. An apparatus, comprising:
- a device configured for advancement along a surgical guide wire, wherein the device comprises:
- a housing through which the surgical guide wire can extend from a proximal aperture of the housing to a distal aperture of the housing;
- a plate within the housing between the proximal and distal apertures and formed with an opening through which the surgical guide wire can extend, the plate being biased to a first orientation, in which the surgical guide wire can move proximally through the opening and is prevented from being moved distally though the opening, the plate being movable to a second configuration, in which the surgical guidewire can move both proximally and distally through the opening; and
- a cap covering the distal aperture of the housing and formed with a hole through which the surgical guidewire can extend, the cap being axially movable relative to the housing and being biased distally relative to the housing.

2. The apparatus of claim 1, wherein the first orientation is an oblique orientation relative to an axis defined between the apertures.

3. The apparatus of claim 1, wherein the plate is biased to the first orientation by a spring.

4. The apparatus of claim 3, wherein the spring is a first spring, and wherein the cap is biased distally by a second spring disposed between the cap and a distal portion of the housing.

5. The apparatus of claim 1, wherein the cap is biased distally by a spring disposed between the cap and a distal portion of the housing.

6. The apparatus of claim 1, comprising:
- a manually manipulable release element to move the plate toward the second orientation.

7. The apparatus of claim 1, wherein movement of the cap relative to the housing absorbs backlash in plate engagement with the surgical guidewire.

8. The apparatus of claim 1, comprising:
- a fulcrum on the housing to limit movement of the plate in a first direction; and
- an extending element on the housing opposite the fulcrum with respect to the plate to limit movement of the plate in a second direction.

9. A medical device, comprising:
- a housing through which a guide wire can extend from a proximal aperture of the housing to a distal aperture of the housing;
- a plate within the housing between the proximal and distal apertures and formed with an opening through which the guide wire can extend, the plate being biased to a first orientation, in which the guide wire can move axially through the opening in only one direction, the plate being movable to a second configuration, in which the guidewire can move axially through the opening in two directions;
- a fulcrum on the housing to limit movement of the plate in a first direction; and
- an extending element on the housing opposite the fulcrum with respect to the plate to limit movement of the plate in a second direction.

10. The medical device of claim 9, comprising:
- a cap covering the distal aperture of the housing and formed with a hole through the surgical guidewire can extend, the cap being axially movable relative to the housing and being biased distally relative to the housing.

11. The medical device of claim 10, wherein the cap is biased distally by a spring disposed between the cap and a distal portion of the housing.

12. The medical device of claim 10, wherein movement of the cap relative to the housing absorbs backlash in plate engagement with the guidewire.

13. The medical device of claim 9, wherein the first orientation is an oblique orientation relative to an axis defined between the apertures.

14. The medical device of claim 9, wherein the plate is biased to the first orientation by a spring.

15. The medical device of claim 9, comprising:
- a manually manipulable release element to move the plate toward the second orientation.

* * * * *